(12) United States Patent
Wise

(10) Patent No.: US 7,655,403 B2
(45) Date of Patent: Feb. 2, 2010

(54) CHD7 GENE POLYMORPHISMS ARE ASSOCIATED WITH SUSCEPTIBILITY TO IDIOPATHIC SCOLIOSIS

(75) Inventor: Carol Wise, Dallas, TX (US)

(73) Assignee: Texas Scottish Rite Hospital for Children, Dallas, TX (US)

( * ) Notice: Subject to any disclaimer, the term of this patent is extended or adjusted under 35 U.S.C. 154(b) by 33 days.

(21) Appl. No.: 11/566,215

(22) Filed: Dec. 2, 2006

(65) Prior Publication Data

US 2008/0131877 A1 Jun. 5, 2008

(51) Int. Cl.
C12Q 1/66 (2006.01)
C12P 19/34 (2006.01)
C07H 21/04 (2006.01)

(52) U.S. Cl. .................. 435/6; 435/91.2; 536/23.5; 536/24.31

(58) Field of Classification Search .................. None
See application file for complete search history.

(56) References Cited

U.S. PATENT DOCUMENTS

| 4,998,531 | A | 3/1991 | Bocchi et al. |
| 5,498,531 | A | 3/1996 | Jarrell |

OTHER PUBLICATIONS

Chorley, Brian et al. Discovery and verification of functional single nucleotide polymorphisms in regulatory genomic regions: current and developing technologies. 2008 Mutation Research vol. 659 pp. 147-157.*
NCBI SNP database entry for the CHD7 gene found online at www.ncbi.nlm.nih.gov/SNP/snp_ref.cgi?chooseRs=all& locusId=55636& mrna=NM_017780.2&ctg=NT_008183.18& prot=NP_060250.2&orien=forward&refresh=refresh accessed online Mar. 20, 2009.*
Abecasis, G. R., et al., "GOLD—Graphical Overview of Linkage Disequilibrium," Bioinformatics, 16:182-183 (2000).
Barral, S., et al., "Precision and type I error rate in the presence of genotype errors and missing parental date: a comparison between the original transmission disequilibrium test (TDT) and TDTae statistics," BMC Genet, 6:S150 (2005).
Bashiardes, S. et al., "SNTG1, the gene encoding γ1-syntrophin: a candidate gene for idiopathic scoliosis," Hum Genet, 115;81-89 (2004).
Benjamini, Y., et al., "Controlling the False Discovery Rate: A Practical and Powerful Approach to Multiple Testing," J Roy Statist Soc, B 57:289-300 (1995).
Benjamini, Y., et al., "Controlling the false discovery rate in behavior genetics research," Behav Brain Res, 125:279-284 (2001).
Boyles, A. L. et al., "Linkage Disequilibrium Inflates Type I Error Rates in Multipoint Linkage Analysis when Parental Genotypes Are Missing," Hum Hered, 59:220-227 (2005).
Chan, V. et al., "A Genetic Locus for Adolescent Idiopathic Scoliosis Linked to Chromosome 19p13.3," Am J Hum Genet, 71:401-406 (2002).

Clayton, D. "A Generalization of the Transmission/Disequilibrium Test for Uncertain-Haplotype Transmission," Am J Hum Genet 65:1170-1177 (1999).
De Kok, J. B., et al., "Rapid Genotyping of Single Nucleotide Polymorphisms Using Novel Minor Groove Binding DNA Oligonucleotides (MGB Probes)," Hum Mutat, 19:554-559 (2002).
Doyle, C. et al., "Scoliosis in CHARGE: A Prospective Survey and Two Case Reports," J Med Genet, 133A:340-343 (2005).
Gordon, D., et al , "A Transmission/Disequilibrium Test That Allows for Genotyping Errors in the Analysis of Single-Nucleotide Polymorphism Data," Am J Hum Genet, 69:371-380 (2001).
Gordon et al. "A transmission disequilibrium test for general pedigrees that is robust to the presence of random genotyping errors and any number of untyped parents," Eur J Hum Genet, 12:752-761 (2004).
Heinemeyer, T., et al, "Databases on transcriptional regulation: TRANSFAC, TRRD and COMPEL," Nucleic Acids Res, 26:364-370 (1998).
Hill W.G., et al, "Maximum-Likelihood Estimation of Gene Location by Linkage Disequilibrium," Am J Hum Genet, 54:705-714 (1994).
Jongmans, M.C. et al "CHARGE syndrome : the pheonotypic spectrum of mutations in the CHD7 gene," J Med Genet, 43:306-314 (2006).
Justice, C. M., et al., "Familial Idiopathic Scoliosis: Evidence of an X-Linked Susceptibiliity Locus," Spine, 28:589-594 (2003).
Kong, A., et al., "Allele-Sharing Models: LOD Scores and Accurate Linkage Tests," J Hum Genet, 61:1179-1188 (1997).
Kruglyak, L., et al , "Parametric and Nonparametric Linkage Analysis: A Unified Multipoint Approach," Am J Hum Genet, 58:1347-1363 (1996).
Lalani, S. R. et al. "Spectrum of CHD7 Mutations in 110 Individuals with CHARGE Syndrome and Genotype-Phenotype Correlation," Am J Hum Genet,. 78.303-314 (2006).
Livak, K. J. "Allelic discrimination using fluorogenic probes and the 5% nuclease assay," Genet Anal, 14:143-149 (1999).
Lohnes, D. "The Cdx1 homeodomain protein: an integrator of posterior signaling in the mouse," Bioessays, 25:971-980 (2003).
Miller N. H. et al. "Identification of Candidate Regions for Familial Idiopathic Scoliosis," Spine, 30:1181-1187 (2005).
Mukhopadhyay, N., et al., "Mega2: data-handling for facilitating genetic linkage and association analyses," Bioinformatics, 21:2556-2557 (2005).
Salehi, L. B. et al. "Assignment of a locus for autosomal dominant idiopathic scoliosis (IS) to human chromosome 17p11," Hum Genet, 111:401-404 (2002).

(Continued)

Primary Examiner—Carla Myers
Assistant Examiner—Amanda Shaw
(74) Attorney, Agent, or Firm—Edwin S. Flores; Chainey P. Singleton; Daniel J. Chalker

(57) ABSTRACT

The present invention includes compositions and methods for diagnosis of polymorphisms associated with susceptibility to idiopathic scoliosis in a patient by determining the presence of a mutation in a nucleic acid sample provided from the patient for a mutation in a transcription factor binding site in one or more non-coding regions of the chromodomain helicase DNA binding protein 7 gene.

8 Claims, 6 Drawing Sheets

OTHER PUBLICATIONS

Sanlaville, D. et al. "Phenotypic spectrum of CHARGE syndrome in fetuses with CHD7 truncating mutations correlates with expression during human development," J Med Genet, 43:211-217 (2006).

Schaid, D. J., et al, "Genotype Relative Risks: Methods for Design and Analysis of Candidate-Gene Association Studies," Am J Hum Genet, 53:1114-1126 (1993).

Spielman, R. S., et al., "Transmission Test for Linkage Disequilibrium: The Insulin Gene Region and Insulin-dependent Diabetes Mellitus (IDDM)," Am J Hum Genet, 52:506-516 (1993).

Subramanian, V., et al., "Disruption of the Murine Homeobox Gene Cdx1 Affects Axial Skeletal Identities by Altering the Mesodermal Expression Domains of Hox Genes," Cell, 83:641-653 (1995).

Terwilliger, J. D. "A Powerful Likelihood Method for the Analysis of Linkage Disequilibrium between Trait Loci and One or More Polymorphic Marker Loci," Am J Hum Genet, 56:777-787 (1995).

Vissers, L. E. et al, "Mutations in a new member of the chromodomain gene family cause CHARGE syndrome," Nat, Genet, 36:955-957 (2004).

Wise C.A. et al. "Localization of Susceptibility to Familial Idiopathic Scoliosis," Spine, 25:2372-2380 (2000).

* cited by examiner

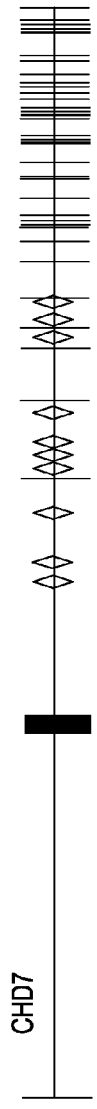
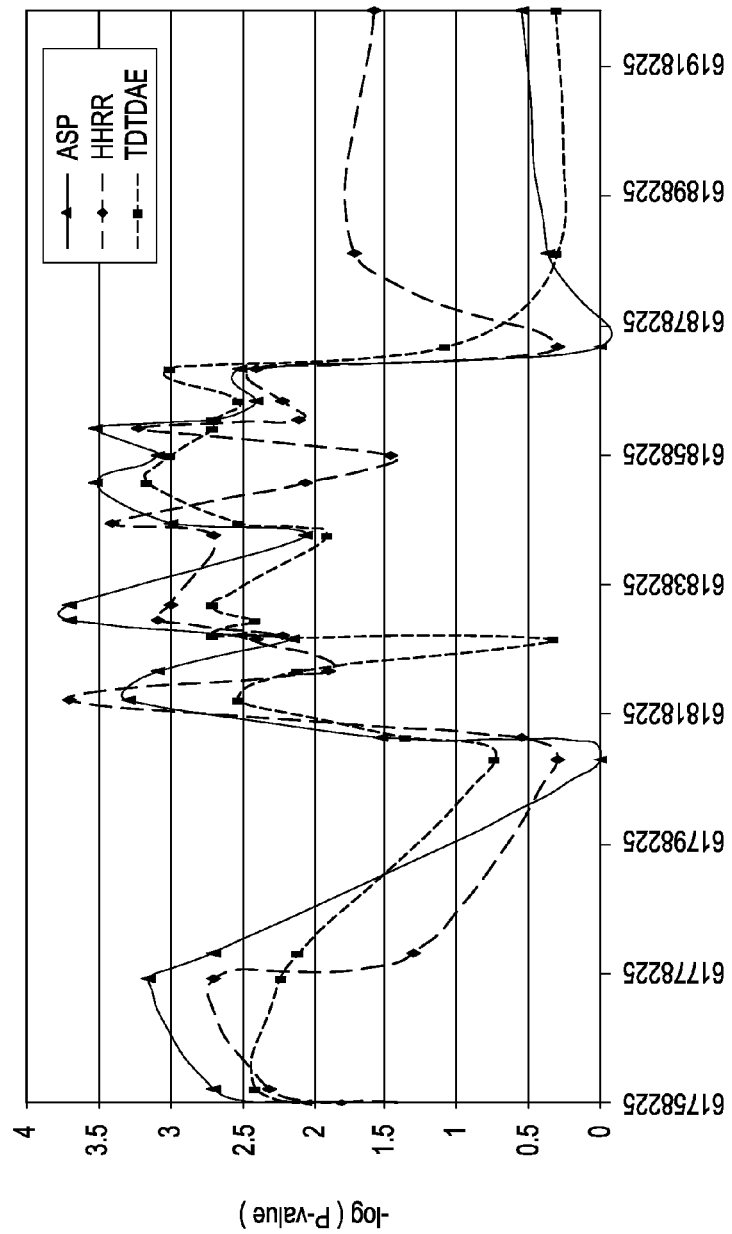
FIG. 4A
FIG. 4B

CHD7 GENE POLYMORPHISMS ARE ASSOCIATED WITH SUSCEPTIBILITY TO IDIOPATHIC SCOLIOSIS

TECHNICAL FIELD OF THE INVENTION

The present invention relates in general to the field of scoliosis, and more particularly, with compositions and methods for the detection of polymorphisms associated with susceptibility to idiopathic scoliosis.

BACKGROUND OF THE INVENTION

Without limiting the scope of the invention, its background is described in connection with scoliosis.

Scoliosis is a lateral deformity of the spine produced by rotation of the vertebral bodies. "Idiopathic" scoliosis occurs in otherwise healthy children, usually during the period of rapid growth at adolescence. It is the most common pediatric spinal deformity and has a prevalence of 2-3% in school age children. Two clear risk factors in IS are remaining growth potential, and female gender[1]. Inheritance is generally complex (MIM #181800), although some families with apparent Mendelian transmission have been described[2]. Genome wide scans in single families and family collections[3-7], and chromosomal breakpoint mapping[8] have tentatively identified several chromosomal regions that may contribute to disease; however, results of these studies have not clearly converged on any single region and IS susceptibility loci have remained elusive.

Despite years of study, few if any methods exist for the diagnosis of scoliosis. One of the few examples is United States Patent Application No. 20060015042, filed by Linial, et al., which teaches a method and apparatus for detection and measurement of scoliosis of the spine. Briefly, a method and apparatus for measuring the lateral curvature of a human spine is taught to detect the presence and degree of scoliosis in the patient. The device is said to be useable by non-medical personnel and medical practitioners, including doctors, chiropractors, physical therapists, nurses and the like. The system is said to be a low cost quick operating hand held device based on the operating structure of a standard computer mouse to determine immediately the curvature of the spine. The hand held device is used to scan the length of a patient's spine by contacting the patient's back as it is drawn along the length of the spine to provide a reading of the lateral curvature as X-Y coordinate information. The X-Y coordinate information is then graphed by a computer software program run on a standard computer. The software program allows repeated readings to be saved and compared over time.

Yet another method for the diagnosis of scoliosis is discussed in United States Patent Application No. 20050130250 by Moreau for a method of diagnosing adolescent idiopathic scoliosis and related syndromes. The method for diagnosing an increased risk for a scoliosis is by measuring dysfunction of the melatonin-signaling pathway in an animal comprising detecting the presence or absence of at least one impairment in melatonin-signaling pathway in at least one of the animal's cells. The presence of one impairment in melatonin-signaling pathway is said to indicate that the animal possesses an increased risk of developing scoliosis. The method of screening includes a compound useful in the treatment of a disease characterized by a dysfunctional melatonin-signaling pathway by contacting a candidate compound with at least one cell expressing at least one melatonin-signaling pathway impairment, wherein the candidate compound is selected if the melatonin signaling pathway impairment is reduced in the presence of the candidate compound as compared to that in the absence thereof.

Despite years of effort toward the diagnosis of pre-existing scoliosis, there exists a need for methods to diagnose scoliosis prior to the onset of symptoms. Early diagnosis of the possibility of scoliosis would permit physicians to monitor, evaluate and correct before or upon the onset of changes is spinal curvature. Early diagnosis is most likely to decrease the effect of the scoliosis, maximize the opportunity for treatment and reduce the length and extent of treatment.

SUMMARY OF THE INVENTION

The present invention includes compositions and methods for diagnosis of polymorphisms associated with susceptibility to idiopathic scoliosis in a patient. One method for diagnosis of polymorphisms associated with susceptibility to idiopathic scoliosis in a patient includes obtaining a nucleic acid sample obtained from the patient and determining the presence of polymorphism in a transcription factor binding site in one or more non-coding regions of the chromodomain helicase DNA binding protein 7 (CHD7) gene, wherein the polymorphism affects transcription factor binding to the cognate transcription factor binding site. The transcription factor binding site may be located between exons 1-7, between exons 2-4 and/or in a 700 base pair fragment known as the conserved block 3. Examples of transcription factors that may bind to sites in the non-coding region of the CHD7 are homeobox transcription factors. In one embodiment, determining the presence or absence of the mutation includes amplifying the chromodomain helicase DNA binding protein 7 gene. Other methods for determining the polymorphism include, e.g., fluorescence in situ hybridization, nuclease protection assay, gel-shift assay, Southern blot analysis, anchor PCR, RACE PCR, ligase chain reaction (LCR), in situ hybridization, immunoprecipitation, immunohistochemistry, Genetic Bit Analysis, primer guided nucleotide incorporation, oligonucleotide ligation assay (OLA) and protein truncation test (PTT), DNA sequencing or RNA sequencing.

Yet another method for detecting polymorphisms associated with susceptibility to idiopathic scoliosis may be a functional method, in which the presence or absence of the mutation is measured by the ability a transcription factor protein to bind to the one or more non-coding regions of the chromodomain helicase DNA binding protein 7 gene from the patient. Alternatively, introns 1-6 of the chromodomain helicase DNA binding protein 7 gene are amplified and the amplicon is used to functionally measure a mutation in the one or more non-coding regions of the chromodomain helicase DNA binding protein 7 gene from the patient by measuring the ability of a transcription factor protein to bind to the amplicon. Transcription factor binding site mutations may be identified by PCR amplification of the chromodomain helicase DNA binding protein 7 gene and nested PCR of overlapping constituent fragments of the chromodomain helicase DNA binding protein 7 gene. The sample may be a body fluid or a tissue that includes cells. The nucleic acids of the sample may be sequenced at the DNA or RNA level to identify changes as compared to the wild type sequence.

Another embodiment of the present invention is a method for diagnosis of polymorphisms associated with susceptibility to idiopathic scoliosis in a patient by determining the effect of a mutation in a nucleic acid sample provided from the patient in a transcription factor binding site in non-coding regions of the chromodomain helicase DNA binding protein 7 gene on gene expression.

In one example, the present invention includes a diagnostic kit for determining susceptibility to idiopathic scoliosis that includes one or more containers one or more probes capable of binding to a mutation in one or more noncoding region of the chromodomain helicase DNA binding protein 7 at a transcription factor binding site. The kit may include probes for transcription factor binding sites located between exons 1-7, between exons 2-4 and/or in a 700 base pair fragment known as conserved block 3. The diagnostic kit may be used to detect the binding to a nucleic acid from a sample is detected by in situ hybridization, PCR, RT-PCR, fluorescence resonance energy transfer, chemiluminescence, enzymatic signal amplification, electron dense particles, magnetic particles, and capacitance coupling. The kit may include those compositions, enzymes and buffers to allow the user to obtain a sample from a patient and have that patient's DNA amplified prior to visualization by direct staining, radiation, chemiluminescence, enzymatic deposition or fluorescence. The probe may be used to detect the target by direct or indirect staining, radiation, chemiluminescence, enzymatic deposition or fluorescence. The probe may even be a transcription factor protein that is detectable directly or indirectly and is specific for one or more non-coding transcription factor binding sites of the chromodomain helicase DNA binding protein 7 gene or a transcription factor protein that is detectable directly or indirectly and is specific for one or more non-coding transcription factor binding sites of the chromodomain helicase DNA binding protein 7 gene and a sample for probe detection has been previously amplified. Another probe may be selected to allow the DNA to be sequenced to identify changes as compared to the wild type sequence.

Another diagnostic kit for identifying one or more mutations in the human the chromodomain helicase DNA binding protein 7 may include one or more containers comprises a pair of primers, wherein one of the primers within the pair is capable of hybridizing directly to, or adjacent to, a noncoding region of the chromodomain helicase DNA binding protein 7 suspected of comprising a transcription factor binding site.

Another embodiment includes a transgenic mouse model for idiopathic scoliosis that includes one or more polymorphisms in the non-coding regions of a chromodomain helicase DNA binding protein 7 gene, wherein the polymorphism affects transcription factor binding to cognate transcription factor binding sites in the non-coding regions. The mouse may be made with a targeting construct with a conditional knock-in, conditional knock-out, gene overexpression, gene underexpression, knock-in, knock-out or combinations thereof. Another transgenic mouse model for idiopathic scoliosis may be constructed by targeting the non-coding regions of the chromodomain helicase DNA binding protein 7 gene. The targeting construct may include one or more polymorphisms in the non-coding regions of the chromodomain helicase DNA binding protein 7 gene. The mouse may be mated with a mouse that is conditionally or permanently deficient in one or more transcription factors suspected of binding to non-coding regions of the chromodomain helicase DNA binding protein 7 gene.

The present invention includes linkage and association of idiopathic scoliosis (IS) with 8q12 loci within the CHD7 gene. Resequencing conserved sequence blocks within over-transmitted haplotypes ($P<10^{-4}$), revealed an associated polymorphism ($P=0.005$) that predicts disruption of a putative cdx transcription factor binding site. It was also found that CHD7 coding mutations cause the CHARGE syndrome of congenital anomalies; furthermore, it is disclosed herein that noncoding CHD7 variants underlie IS susceptibility.

BRIEF DESCRIPTION OF THE DRAWINGS

For a more complete understanding of the features and advantages of the present invention, reference is now made to the detailed description of the invention along with the accompanying figures and in which:

FIG. 4A. The CHD7 genomic region is shown above with exons indicated in blue and intronic conserved sequence blocks shown in red. FIG. 4B is a plot of linkage and transmission disequilibrium P-values for 23 SNPs in the CHD7 gene. $-\log 10$ P values are plotted along the Y axis versus physical position along the X axis for each SNP.

DETAILED DESCRIPTION OF THE INVENTION

Figure 1:
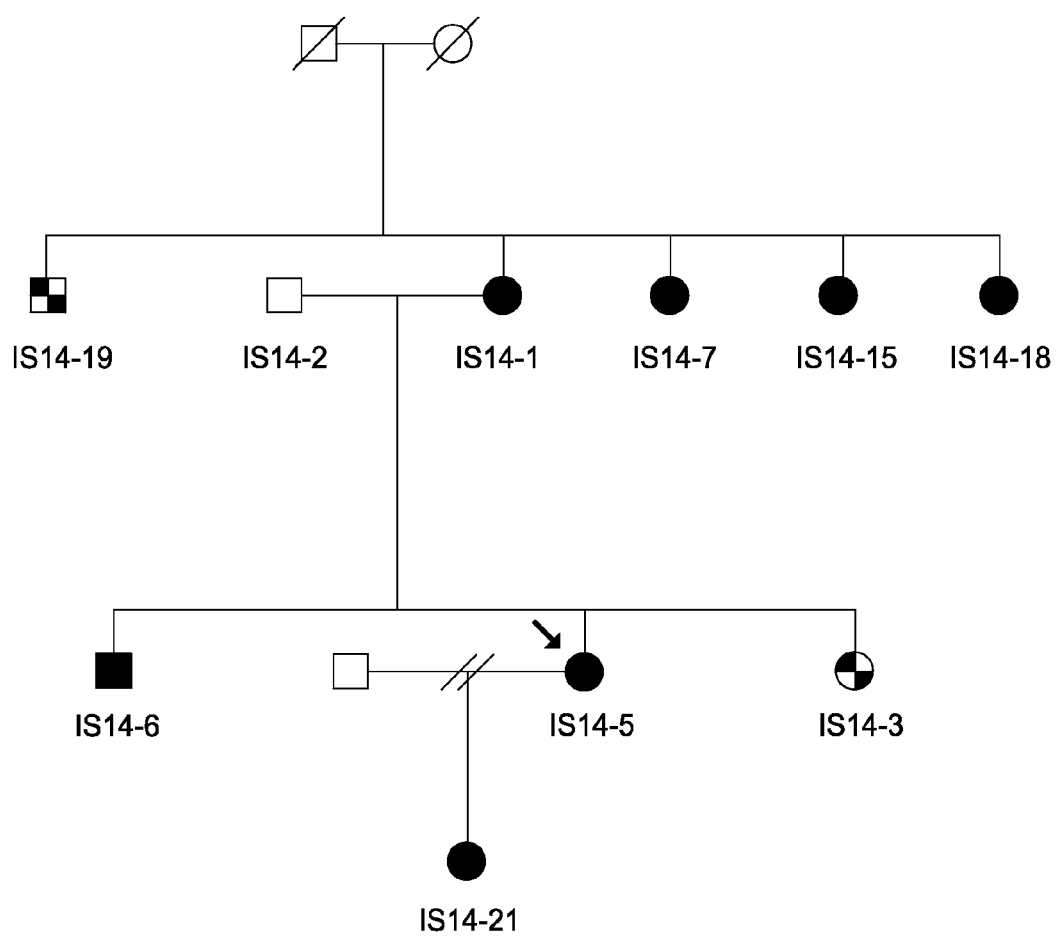
FIG. 1. Pedigree of family IS14. Blackened symbols indicate affected individuals. Cross-hatches denote individuals with mild scoliosis (<15° Cobb angle) that were scored as "unknown" in subsequent analyses.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the terms "allele" and "allelic variant" refer to alternative forms of a gene including introns, exons, intron/exon junctions and 3' and/or 5' untranslated regions that are associated with a gene or portions thereof. Generally, alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. The term "allelic variant of a polymorphic region of a gene" refers to intronic or exonic regions of a gene, e.g., a chromodomain helicase DNA binding protein 7 (CHD7) gene having one or several nucleotide sequences found in that region of the gene in other individuals. Genes may exist in single or multiple copies within the genome of an individual. Such duplicate genes may be identical or may have certain modifications, including nucleotide substitutions, additions or deletions, which all still code for polypeptides having substantially the same activity. Allelic differences may or may not result in differences in amino acid sequence of the encoded polypeptide, yet still encode a polypeptide with the same biological activity.

As used herein, the terms "biological activity" or "bioactivity" or "activity" or "biological function", are used interchangeably and refer to the direct or indirect involvement of the polymorphism in a clinical outcome that is directly or indirectly related to mutations in intronic regions a chromodomain helicase DNA binding protein 7 gene, or by any subsequence thereof. Changes in biological activities include, e.g., changes in gene expression, transcript stability, protein binding, chromosomal stability, nucleosome formation, histone binding, promoter, suppressor and enhancer binding and the like. In one example, the intronic regions of the CHD7 gene may affect an upstream region of a gene, which is regulated by the same or a different transcription factor or the formation, winding or unwinding of a nucleosome.

As used herein, the term "aberrant" or "mutant", as applied to the CHD7 gene refers to an activity that differs from the activity of the wild-type or native gene or which differs from the activity of the polypeptide in a healthy subject and leads alone or in combination with other genetic disorders to idiopathic scoliosis, e.g., a decrease or change in its expression due to changes in non-coding regions.

As used herein, the term "nucleotide sequence complementary to the nucleotide sequence set forth in SEQ ID NO.: X" refers to the nucleotide sequence of the complementary strand of a nucleic acid strand having SEQ ID NO.: X. The nucleic acid sequence for CHD7, is GeneID 55636 and Genbank accession no. is NM_017780.2, which are incorporated herein by reference. The term "complementary strand" is used herein interchangeably with the term "complement" of a nucleic acid strand that includes a coding and a non-coding strand. When referring to double stranded nucleic acids, the complement of a nucleic acid having SEQ ID NO.: X refers to the complementary strand of the strand having SEQ ID NO.: X or to any nucleic acid having the nucleotide sequence of the complementary strand of SEQ ID NO.: X. When referring to a single stranded nucleic acid having the nucleotide sequence SEQ ID NO.: X, the complement of this nucleic acid is a nucleic acid having a nucleotide sequence which is complementary to that of SEQ ID NO.: X. The nucleotide sequences and complementary sequences thereof are always given in the 5' to 3' direction.

As used herein, the terms "homology" or "identity" or "similarity" refer to sequence similarity between two polypeptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences.

As used herein, the term "isolated" as used herein with respect to nucleic acids, such as DNA or RNA, refers to molecules separated from other DNAs, or RNAs, respectively, that are present in the natural source of the macromolecule. For example, an isolated nucleic acid for CHD7 refers to the nucleic acid sequence that includes exons, introns and the regions that flank the CHD7 gene in genomic DNA. The term isolated as used herein also refers to a nucleic acid or peptide that is substantially free of cellular material or culture medium when produced by recombinant DNA techniques, or chemical precursors or other chemicals when chemically synthesized. Moreover, an "isolated nucleic acid" may include nucleic acid fragments that are not naturally occurring as fragments and would not be found in the natural state, e.g., when the CHD7 genomic DNA or portions thereof are placed in a vector (e.g., a plasmid or virus) or on a substrate (e.g., a microarray).

As used herein, the term "modulation" as used herein refers to both upregulation (i.e., activation or stimulation (e.g., by agonizing or potentiating)) and downregulation (i.e. inhibition or suppression (e.g., by antagonizing, decreasing or inhibiting)) of the CHD7 gene or proteins that are associated with the gene, e.g., transcription factors, histones and the like.

As used herein, the term "mutated gene" refers to an allelic form of a gene that is capable of altering the phenotype of a subject having the mutated gene relative to a subject which does not have the mutated gene, namely, idiopathic scoliosis. If a subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between that of a homozygous and that of a heterozygous subject (for that gene), the mutation is said to be co-dominant. As with disease conditions that require one or more changes in the genome to lead to disease, the mutations and changes that are associated with idiopathic scoliosis is expected to include other genes that may affect the penetrance of the changes to the non-coding regions of CHD7.

As used herein, the term "non-human animals" of the invention include mammals such as rodents, non-human primates, sheep, dog, cow, chickens, amphibians, reptiles, etc. Non-human animals are selected from the rodent family including rat and mouse, most preferably mouse, though transgenic amphibians, such as members of the *Xenopus* genus, and transgenic chickens can also provide important tools for understanding and identifying agents which can affect, for example, embryogenesis and tissue formation. The term "chimeric animal" is used herein to refer to animals in which the recombinant gene is found, or in which the recombinant gene is expressed in some but not all cells of the animal. The term "tissue-specific chimeric animal" indicates that one of the recombinant CHD7 genes is present and/or expressed or disrupted in some tissues but not others.

As used herein, the term "nucleic acid" refers to polynucleotides or oligonucleotides such as deoxyribonucleic acid (DNA), and, where appropriate, ribonucleic acid (RNA), equivalents and analogs of either RNA or DNA made from nucleotide analogs and as applicable to the embodiment being described, single (sense or antisense) and double-stranded polynucleotides.

As used herein, the term "polymorphism" refers to the coexistence of more than one form of a nucleic acid, including exons and introns, or portion (e.g., allelic variant) thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long. A "polymorphic gene" refers to a gene having at least one polymorphic region.

As used herein, the term "promoter" refers to a DNA sequence that regulates expression of a selected DNA sequence operably linked to the promoter, and which effects expression of the selected DNA sequence in cells. The term encompasses "tissue specific" promoters, are those promoters that effect expression of the selected DNA sequence only in specific cells (e.g., cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

As used herein, the terms "protein", "polypeptide" and "peptide" are used interchangeably herein when referring to a gene product.

As used herein, the term "transcriptional regulatory sequence" is a generic term used throughout the specification to refer to DNA sequences, such as initiation signals, enhancers, and promoters, which induce or control transcription of protein coding sequences with which they are operably linked. In one embodiment, transcription of the CHD7 genes is under the control of a promoter sequence (or other transcriptional regulatory sequences) that controls the expression of the recombinant gene in a cell-type in which expression is intended and/or at different times during development, the growth phase of an individual and/or in certain tissues or cells within a tissue.

As used herein, the term "transfection" refers to the introduction of a nucleic acid, e.g., via an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a form of the CHD7 gene.

As used herein, the term "transgene" refers to a nucleic acid sequence that includes at least a portion of the CHD7 gene. A transgene could be partly or entirely heterologous, i.e., foreign, to the transgenic animal or cell into which it is introduced, or, can be homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for changes to the expression or binding of transcription factors that bind to intronic portions of the CHD7 gene.

As used herein, the term "transgenic animal" refers to any non-human mammal, bird or an amphibian, in which one or more of the cells of the animal contain heterologous nucleic acid introduced by way of human intervention, such as by transgenic techniques well known in the art. One or more mutants of the CHD7 gene are introduced into the cell, directly or indirectly by introduction into a precursor of the cell, by way of deliberate genetic manipulation, such as by microinjection or by infection with a recombinant virus. The term genetic manipulation may include classical cross-breeding, or in vitro fertilization, when mating a transgenic to a non-transgenic animal to the extent that the transgene was previously introduced into one of the mating partners. Mutants of the CHD7 molecule may be integrated within a chromosome, or it may be extrachromosomally replicating DNA. In the typical transgenic animals described herein, the transgene causes one or more symptoms associated with idiopathic scoliosis. However, transgenic animals in which the recombinant CHD7 gene is silent are also contemplated, as for example, the FLP or CRE recombinase-dependent constructs. Moreover, "transgenic animal" also includes those recombinant animals in which gene disruption of one or more transcription factor genes is caused by human intervention, including both recombination and antisense techniques. When using homologous recombination to introduce changes into the genome or a host animal, it is possible to produce a traditional knock-out, where the target portion is eliminated or rendered non-functional and/or a knock-in, where the target portion is reintroduced and/or its expression is modified.

As used herein, the term "vector" refers to a nucleic acid molecule, which is capable of transporting another nucleic acid to which it has been linked. One type of preferred vector is an episome, i.e., a nucleic acid capable of extra-chromosomal replication. Vectors are those nucleic acids capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

As used herein, the term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

Numerous methods for the detection of polymorphisms are known and may be used in conjunction with the present invention. Generally, these include the identification of one or more mutations in the underlying nucleic acid sequence either directly (e.g., in situ hybridization) or indirectly (identifying changes to a secondary molecule, e.g., protein sequence or protein binding).

One well-known method for detecting polymorphisms is allele specific hybridization using probes overlapping the mutation or polymorphic site and having about 5, 10, 20, 25, or 30 nucleotides around the mutation or polymorphic region. For use in a kit, e.g., several probes capable of hybridizing specifically to allelic variants, such as single nucleotide polymorphisms, are provided for the user or even attached to a solid phase support, e.g., a bead or chip.

Another method for detecting polymorphisms includes using the probe/primer in a polymerase chain reaction (PCR) (see, e.g. U.S. Pat. Nos. 4,683,195 and 4,683,202), such as anchor PCR or RACE PCR, or, alternatively, in a ligase chain reaction (LCR). Briefly, the method includes the steps of (i) collecting a sample of cells from a patient, (ii) isolating genomic nucleic acid from the cells of the sample, (iii) contacting the nucleic acid sample with one or more primers which specifically hybridize to non-coding regions of the CHD7 gene under conditions such that hybridization and amplification of the non-coding regions of the CHD7 gene (if present) occurs, and (iv) detecting the presence or absence of an amplification product, or detecting the size of the amplification product and comparing the length to a control sample. It is anticipated that PCR, LCR or any other amplification procedure (e.g. self sustained sequence replication (Guatelli, J. C. et al., 1990, Proc. Natl. Acad. Sci. USA 87:1874-1878), transcriptional amplification system (Kwoh, D.Y. et al., 1989, Proc. Natl. Acad. Sci. USA 86:1173-1177), or Q-Beta Replicase (Lizardi, P. M. et al., 1988, Bio/Technology 6:1197)), may be used as a preliminary step to increase the amount of sample on which can be performed, any of the techniques for detecting mutations described herein.

Another method for detecting polymorphisms is the identification of alterations in restriction enzyme cleavage patterns. For example, sample and control DNA is isolated, amplified (optionally), digested with one or more restriction endonucleases, and fragment length sizes are determined by gel electrophoresis. One such method includes the use of sequence specific ribozymes (see, for example, U.S. Pat. No. 5,498,531) that can detect the presence of specific mutations by development or loss of a ribozyme cleavage site.

Any of a number of sequencing methods known in the art can be used to directly sequence the relevant portions of the CHD7 gene and detect mutations by comparing the sequence of the sample with the corresponding wild-type (control) sequence. Exemplary sequencing reactions include those based on techniques developed by Maxim and Gilbert or Sanger, which may be accomplished using automated sequencing procedures and equipment.

Another method is protection from cleavage agents (such as a nuclease, hydroxylamine or osmium tetroxide and with piperidine) can be used to detect mismatched bases in RNA/RNA or RNA/DNA or DNA/DNA heteroduplexes (Myers, et al. (1985) Science 230:1242). In general, the art technique of "mismatch cleavage" starts by providing heteroduplexes formed by hybridizing (labelled) RNA or DNA containing the wild-type genomic CHD7 sequence with potentially mutant RNA or DNA obtained from a tissue sample. The double-stranded duplexes are treated with an agent that cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. Either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation.

Another method of detecting polymorphisms is the alteration in electrophoretic mobility, e.g., single strand conformation polymorphism (SSCP) may be used to detect differences in electrophoretic mobility between mutant and wild type nucleic acids (Orita et al. (1989) Proc Natl. Acad. Sci. USA 86:2766, see also Cotton (1993) Mutat Res 285:125-144; and Hayashi (1992) Genet Anal Tech Appl 9:73-79). Single-stranded DNA fragments of sample and control CHD7 nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. A related method detect the movement of mutant or wild-type fragments in polyacrylamide gels containing a gradient of denaturant is assayed using denaturing gradient gel electrophoresis (DGGE).

Detecting point mutations and/or the identity of the allelic variant of a polymorphic region may include, e.g., selective oligonucleotide hybridization, selective amplification, or selective primer extension. Allele-specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labeled target DNA.

Allele-specific amplification technology that depends on selective PCR amplification may also be used. Briefly, oligonucleotides used as primers for specific amplification that carry the mutation or polymorphic region of interest in the center of the molecule (so that amplification depends on differential hybridization) or at the extreme 3' end of one primer where, under appropriate conditions, mismatch can prevent, or reduce polymerase extension may be used. A novel restriction site in the region of the mutation may also be used to create cleavage-based detection. Other related techniques include the use of amplification using Taq ligase for amplification. In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described in, e.g., U.S. Pat. No. 4,998,617, relevant portions incorporated herein by reference. Briefly, the OLA protocol uses two oligonucleotides that are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., Proc. Natl. Acad. Sci. (U.S.A.) 87:8923-8927 (1990). In this method, PCR is used to achieve the exponential amplification of target DNA, which is then detected using OLA. The OLA procedure may also be used in conjunction with florescence resonance energy transfer (FRET) probe methods and compounds.

Another method for detection of single base polymorphisms is by using a specialized exonuclease-resistant nucleotide, as disclosed in, e.g., U.S. Pat. No. 4,656,127, relevant portions incorporated herein by reference. Briefly, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. The incorporation renders the primer resistant to exonuclease, and thereby permits its detection.

The methods described herein may be performed, for example, by utilizing pre-packaged diagnostic kits that include at least one probe nucleic acid, primer set; one or more detectable transcription factor and/or antibody reagent described herein, which may be conveniently used, e.g., in clinical settings to diagnose patients exhibiting symptoms or family history of a disease or illness involving a mutation in the non-coding regions of CHD7.

Any cell type or tissue may be use for diagnosis, e.g., a bodily fluid, e.g., blood, is obtained from the subject to determine the presence of a mutation or the identity of the allelic variant of a polymorphic region of non-coding regions of the CHD7 gene. Test can be performed from any bodily fluid that includes genomic DNA, e.g., blood, tissue biopsies, hair follicles or skin. For prenatal diagnosis, fetal nucleic acid samples can be obtained from maternal blood, amniocytes or chorionic villi may be obtained for performing prenatal testing.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, N.Y.).

In addition to methods which focus primarily on the detection of one nucleic acid sequence, profiles may also be assessed in such detection schemes. Fingerprint profiles may be generated, for example, by using a differential display procedure, Northern analysis.

For use with the present invention a number of in silico methods may be used to identify known and potential sites for polymorphisms that affect the binding of proteins to nucleic acids. One such software for the identification of transcription and other DNA binding sites may be, e.g., those methods taught by Thompson, et al., Gibbs Recursive Sampler: finding transcription factor binding sites Nucleic Acids Res. 2003 Jul. 1; 31(13): 3580-3585. The Gibbs Motif Sampler is a software package for locating common elements in collections of biopolymer sequences. In this paper we describe a new variation of the Gibbs Motif Sampler, the Gibbs Recursive Sampler, which has been developed specifically for locating multiple transcription factor binding sites for multiple transcription factors simultaneously in unaligned DNA sequences that may be heterogeneous in DNA composition. Here we describe the basic operation of the web-based version of this sampler. The sampler may be accessed at bayesweb.wadsworth.org/gibbs/gibbs.html and at www.bioinfo.rpi.edu/applications/bayesian/gibbs/gibbs.html. An online user guide is available at bayesweb.wadsworth.org/gibbs/bernoulli.html and at www.bioinfo.rpi.edu/applications/bayesian/gibbs/manual/bernoulli.html. Solaris, Solaris.x86 and Linux versions of the sampler are available as stand-alone programs for academic and not-for-profit users. Commercial licenses are also available. The Gibbs Recursive Sampler is distributed in accordance with the ISCB level 0 guidelines and a requirement for citation of use in scientific publications.

Materials and methods. Research subjects. All participating research subjects were ascertained under a protocol approved by the University of Texas Southwestern Medical Center Institutional Review Board. Families were ascertained through affected probands presenting in pediatric orthopaedic clinics and reporting additional family history of idiopathic scoliosis (IS). Greater than 95% of the 53 families were referred through collaborating physicians at Texas Scottish Rite Hospital for Children (TSRHC) in Dallas, Tex. Affected probands were invited to participate by providing health history, family history of musculoskeletal disease, diagnostic information including radiographs, and a blood sample. Probands continued to be followed clinically regardless of participation in the study. Diagnostic and inclusion criteria are addressed below.

Additional family members were ascertained through the participating probands. For those reporting history of scoliosis we required documentation by health history and standing anteroposterior X ray. Most of these potentially affected individuals (46 of 77) were also current or former patients diagnosed and treated at TSRHC. All such medical record information and X rays were reviewed by a single orthopaedic surgeon (JAH). Other connecting family members, either reporting negative history of IS, or without documenting records and X rays, were collected and treated as "unknown diagnosis".

Diagnosis. Positive diagnosis required radiographic observation of a lateral deformity of the spine of at least 10° with otherwise normal vertebral bodies. Exclusions were extensive and included trauma or co-existing disorders that often involve scoliosis, such as cerebral palsy, spinal muscular atrophy, Marfan's, Ehler's Danlos, Charcot-Marie-Tooth, neurofibromatosis, spina bifida, etc. Patients that fit the diagnosis of IS but with left thoracic curves or with abnormal neurological signs were typically screened by magnetic resonance imaging (MRI) of the neuraxis to rule out conditions such as syringomyelia.

Inclusion criteria. Scoliosis is defined as a lateral deviation >10° as measured by the Cobb angle method[1]. Because the purpose was to identify susceptibility loci, for this study we included affected probands and connecting family members without regard to curve severity. To minimize false positives, we included subjects with a minimum requirement of 15° as measured from standing spinal radiographs. Those with mild curves less than 15 degrees were given "unknown" diagnosis in all subsequent analyses (below). Any families with history of disease that could involve scoliosis, for example Marfan's syndrome or Duchenne muscular dystrophy, were excluded from the study. Families reporting other musculoskeletal deformities (i.e. hyperkyphosis or clubfeet) were also excluded. Milder curve measurements ($\leqq 25$ degrees) were re-measured by a single orthopedic surgeon (JAH). All families included in this study were of European descent. From this set we initially selected 53 multiplex families for the purpose of increasing power to detect linkage between IS and selected loci. We note that family IS9, in which we had previously performed a genome wide linkage scan[2], was not included in this study.

Age of first presentation, curve progression, growth rate, treatment modalities, ethnicity, county of residence, treating physician, and family history were documented for all affected individuals. For the 53 multiplex family cohort, 130 were affected with IS, with curve severities ranging from 15 to 113 degrees and averaging 40.5 degrees; age of first presentation was approximately 11.5 years, and 86% were ascertained via female probands.

Genotyping. Genomic DNA was isolated from whole blood by standard procedures. Peripheral blood lymphocytes were also prepared from selected affected individuals and cryostored for establishment of lymphoblastoid cell lines. For the genome wide scan in family IS14, polymorphic microsatellite loci evenly spaced at 10-15 cM intervals across all autosomes were genotyped using an ABI 377 sequence analysis system as previously described[2]. For follow-up studies, polymorphic microsatellite loci from candidate regions were likewise genotyped in DNA samples of the other 52 multiplex families. All such genotypes were examined by at least two individuals independently. Single nucleotide polymorphic (SNP) loci were selected for fine mapping studies of the CHD7 gene. Fifteen SNPs were initially chosen to be approximately evenly spaced throughout the CHD7 gene and with reported minor allele frequencies $\geq 0.05$ in Caucasian population. Ten additional SNPs were subsequently selected from within the ~93 kb region producing evidence of association with IS. All except two polymorphic markers were selected using publicly available information as reported by (www.ncbi.nlm.nih.gov) or (genome.ucsc.edu/cgi-bin/hg-Gateway). Three SNPs, hcv148921, hcv509504, and hcv509505, were selected using (marketing.appliedbiosystems.com/mk/get/snpb_Login?source=cd). SNP genotyping was performed by amplifying 20 ng genomic DNA in Taqman® allele discrimination assays (Applied Biosystems). Custom Taqman probes[3] for each allele were designed using Primer Express® v2.0 software (Applied Biosystems) according to recommended guidelines[4]. Genotyping and analysis were performed using an ABI Prism® 7900HT system.

Statistical analyses. For all analyses of polymorphisms described below, allele frequencies were calculated from the data using the method implemented in the RECODE program (watson.hgen.pitt.edu/register/). Because our goal was to identify genes underlying IS susceptibility, and because a range of curve severities is common within families, we did not attempt to distinguish quantitative differences but instead included everyone with curves $\geq 15°$ in a single liability class.

Linkage analyses of microsatellite loci. For the genome wide scan of family IS14, two point LOD scores were calculated by the MLINK program in the LINKAGE package using a disease frequency of 0.01[5]. Nonparametric lod (NPL) scores of the same data were generated using Genehunter[6]. Follow-up analysis of 8q loci in the other 52 families was performed using the statistical method of Kong and Cox (KAC)[7]. This statistic is normally distributed under the null hypothesis of no linkage. Transmission disequilibrium was measured using the Transmission Disequilibrium Test allowing for errors (TDTae) as implemented in the TDTAE program[8,9]. The TDTae method is robust to missing parental genotype data or errors that may be introduced with genotyping microsatellite loci. In this analysis we used the multiplicative model for TDTae; that is, the genotype relative risk for the homozygous genotype was constrained to be the square of the genotype relative risk for the heterozygote genotype, making the statistic equivalent to the original TDT statistic[10] when both parents are genotyped. Results of the TDTae are reported with correction for tests at multiple alleles. The False Discovery Rate (FDR) method[11,12] was applied to the final data set as further correction for tests at multiple loci as described below.

Fine-mapping studies of the CHD7 gene. Consistency with Hardy-Weinberg equilibrium was verified for all SNP genotypes. Genetic distances for SNPs were interpolated from physical locations (assembly hg18) as given in the University of Santa Cruz (UCSC) genome browser (genome.ucsc.edu/cgi-bin/hgGateway) or National Center for Biotechnology website (www.ncbi.nlm.nih.gov). To fine-map the trait locus, we genotyped 25 SNPs in the CHD7 gene in 53 IS families. As noted above (Genotyping), two of the SNPs were not sufficiently polymorphic and were dropped from all further analyses. That is, in our statistical analyses we only considered 23 SNPs. For our single-locus analyses, we considered three genetic model-free methods: (i) The Affected Sib Pair (ASP) method as implemented in the ANALYZE program[13,14]; (ii) The Haplotype-Based Haplotype Relative Risk Test (HHRR) as implemented in the ANALYZE program[13,15]; (iii) and The Transmission Disequilibrium Test Allowing for Errors (TDTae)[8,9] as implemented in the TDTAE program. Each of the three statistics complements the other; the ASP statistic tests for linkage and does not use information on linkage disequilibrium (LD); the HHRR statistic is a test of association (that is, it tests whether there is preferential transmission of a given allele to affected offspring across families); and the TDTAE is a test of linkage in the presence of association that also provides estimates of genotype relative risks (GRR)[16]. While we did not observe any genotyping errors in these data, we used the TDTae statistic nonetheless, since it is also robust to missing parental genotype information[9,17]. We used the multiplicative model specification with the TDTae method and restricted our attention to those markers with observed minor allele frequencies greater than 0.05. We computed levels of LD, as determined by the squared correlation coefficient $\Delta^2$ [18,19] for all pairs of the 23 SNPs using the fine mapping pedigree data. These coefficients were computed using the method implemented in the GOLD software[20].

For multipoint analyses, as with the two-point analyses, we used two genetic model free methods: (i) the affected relative pair method Zlr, as implemented in the GENEHUNTER-PLUS program[6,7]; and (ii) the multi-locus TDT statistic, implemented in the TRANSMIT program (v 2.1)[6,21]. As with the two-point methods, the Zlr method tests for linkage, while the TDT tests for linkage in the presence of association. Formatting of all pedigree data for multipoint analyses was facilitated through use of the Mega2 program[22]. For (i), multipoint linkage analysis was performed using all 23 markers. However, there is inter-marker LD and linkage statistics that may inflate the false positive rates in the presence of missing parental genotype information[23]. The maximum Zlr statistic of 2.63 (P=0.004) occurred for marker rs4738813 at position 10.361. The remaining markers all had Zlr statistics on the order of 2.35 (P=0.009) (full results not shown). For (ii), two- and four-locus TDT statistics were considered. Haplotypes and their frequencies were estimated via maximum likelihood as implemented in TRANSMIT. Due to computation constraints, all consecutive four-locus haplotype TDT statistics were computed in a "sliding window" fashion. That is, each multi-locus TDT statistic was computed using ordered SNPs 1-4, then for SNPs 4-7, 7-10, etc. The last set of four loci considered were SNPs 19-22. Also computed were a two-locus TDT statistic using SNPs 22 and 23. To be consistent with the single locus TDT analyses, only haplotypes whose estimated frequency was greater than 5% were considered. The maximum TDT statistic was selected. Specifically, for each haplotype transmitted in a four-locus (or two-locus) set, there is a corresponding TDT statistic and p-value. The maximum of the set of TDT statistics for each set of observed haplotypes in the four loci (or two loci) was selected and computed P-values computed for the maximum TDT statistic in each set of four SNPs by creating 50,000 bootstrap samples and computing the proportion of bootstrap samples in which the maximum TDT statistic exceeded that of the maximum TDT statistic for the observed data.

To combine P-values for SNPs that were in more than one set of loci (e.g., SNP 4, SNP 7, SNP 10, etc), we computed the average of transformed P-values. For example, if the max TDT statistic P-value for the first set of SNPs containing SNP 4 is $p_1$ and the p-value for the max TDT statistic p-value for the second set of SNPs containing SNP 4 is $p_2$, then the transformed p-value is $(-\log(p_1) + -\log(p_2))/2$. Application of single locus and multi-locus TDT statistics produced a total of 70 TDT P-values.

Correction for multiple testing with TDT methods using False Discovery Rate. To correct for the numerous TDT tests performed, we used a variation of the False Discovery Rate (FDR) method[11] that allows for correlated data[12]. Specifically, for the 70 TDT tests performed (single locus and multi-locus), we determined the FDR threshold by sorting the test P-values $p_i$ for i between 1 and 286 and re-labeled the sorted P-values as $p_{(i)}$ so that $p_{(1)} \leq p_{(2)} \ldots \leq p_{(286)}$. If we let $t_i = \min(\alpha, 286 \times \alpha/(287-i)^2)$ (where $\alpha$ is the significance level; 0.05 in this case), then we declare those P-values $p_{(i)}$ that satisfy the property $p_{(i)} \leq t_i$ to be significant after correction for multiple testing. The FDR threshold for TDT analyses was computed to be $1.9 \times 10^{-4}$.

Measures of pairwise LD. Specifically, the set of three consecutive SNP markers 15-16-17 all displayed pair-wise correlation ($\Delta^2$) values close to 1. The pair-wise $\Delta^2$ values for the pairs 15-16, 15-17, and 16-17 were 0.892, 0.897, and 0.773, respectively, with a minimum chi-square value of 53.97 (1 df) ($P = 2.0 \times 10^{-13}$).

Genotype relative risk (GRR) estimates. The genotype relative risks were generated using TDTAE software[13,14] and are defined as follows:

$R_i = \Pr(\text{i copies of risk allele in disease locus genotype})/\Pr(0$ copies of risk allele in disease locus genotype), $i = 1, 2$.

DNA resequencing. To optimize the probability of detecting risk alleles we selected probands that were homozygous for the majority of overtransmitted alleles for SNPs 2-20. Selected regions of the CHD7 gene were amplified from DNA samples of the 25 affected cases and 44 parental controls via the polymerase chain reaction (PCR) (primer sequences and PCR conditions available upon request). Amplicons were analyzed by direct DNA capillary sequencing using a 3730 XL (Applied Biosystems) instrument. Chromatograms were searched for heterozygous variants with sequencing analysis 5.1.1 software utilizing the included KB base caller. All sequences were aligned using the Sequencher program (Genecodes) and compared to reference human sequence (hg18) from publicly available databases reported at (genome.ucsc.edu/cgi-bin/hgGateway) or (www.ensembl.org).

Comparative sequence analyses. Reference human CHD7 genomic sequence was compared to other vertebrate (mouse, rat, rabbit, dog, armadillo, elephant, opossum, chicken) CHD7 sequences using the UCSC conservation track. Regions showing evidence of sequence conservation between multiple vertebrate species were analyzed further for potential variation using SNPBLAST available at the NCBI website. Similarity to consensus transcription factor binding sites sequences was identified using TFSEARCH (24). In these analyses, results were restricted to searches of vertebrate species and that surpassed a threshold score of 85.0.

Figure 2:
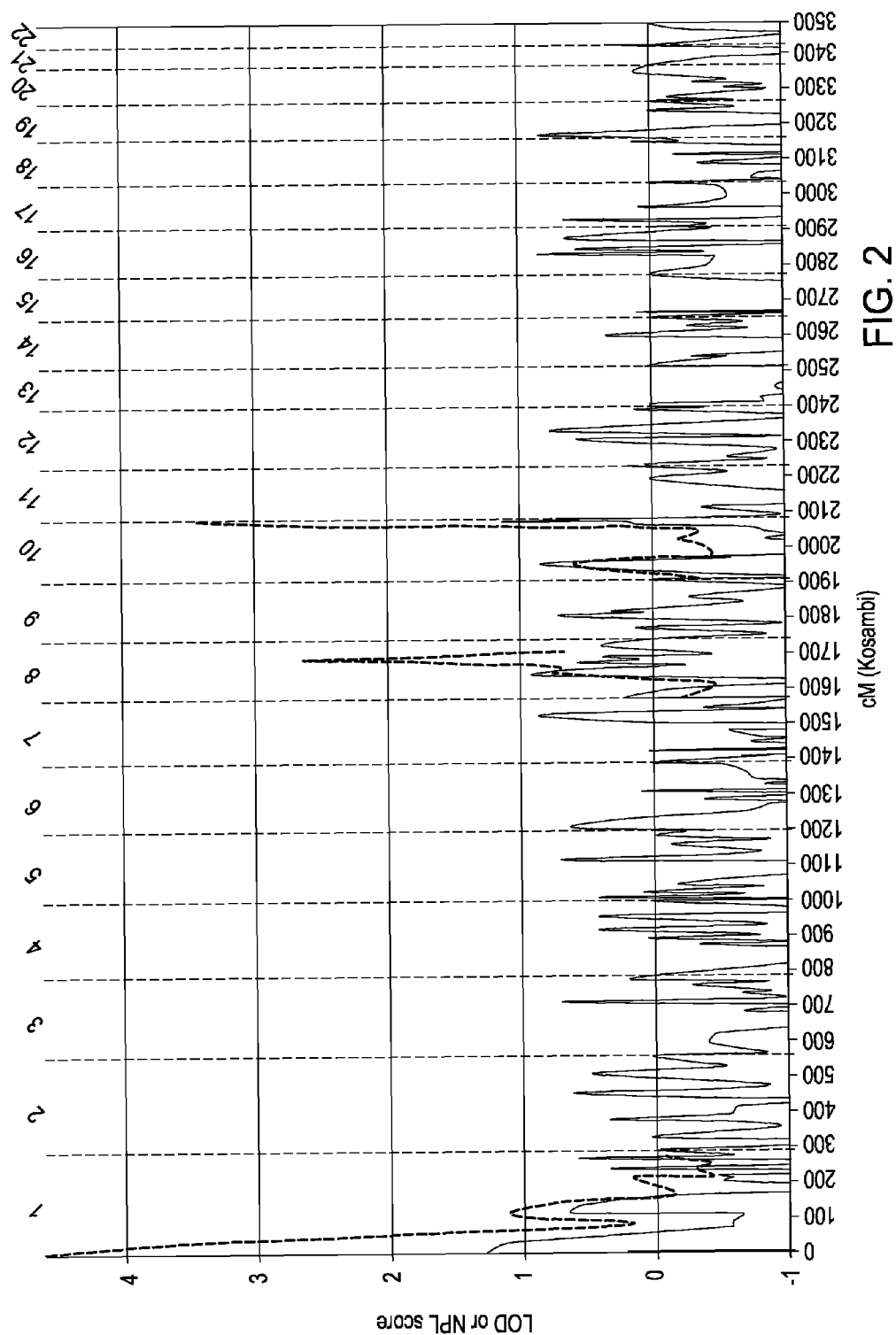
FIG. 2. Results of genomewide scan in family IS14. Distance across chromosomes is plotted on the X axis versus results of linkage analysis along the Y axis. Resulting LOD score for parametric analyses in which we considered only affected individuals and dominant inheritance are plotted as solid lines for each chromosome. Maximal results were obtained from chromosomes 1, 8, and 10. The top three non-parametric lod (NPL) scores also occurred for chromosomes 1, 8, and 10 and are overlaid and plotted as dashed lines.

Results. Multiplex families were ascertained via probands with adolescent-onset scoliosis and no other co-existing diagnoses. All participating research subjects were ascertained under a protocol approved by the University of Texas Southwestern Medical Center Institutional Review Board. A genome wide linkage scan in one extended family IS14 produced modest linkage peaks for several regions including chromosomes 1p, 8q, and 10q (FIG. 1 and FIG. 2).

Figure 3A:
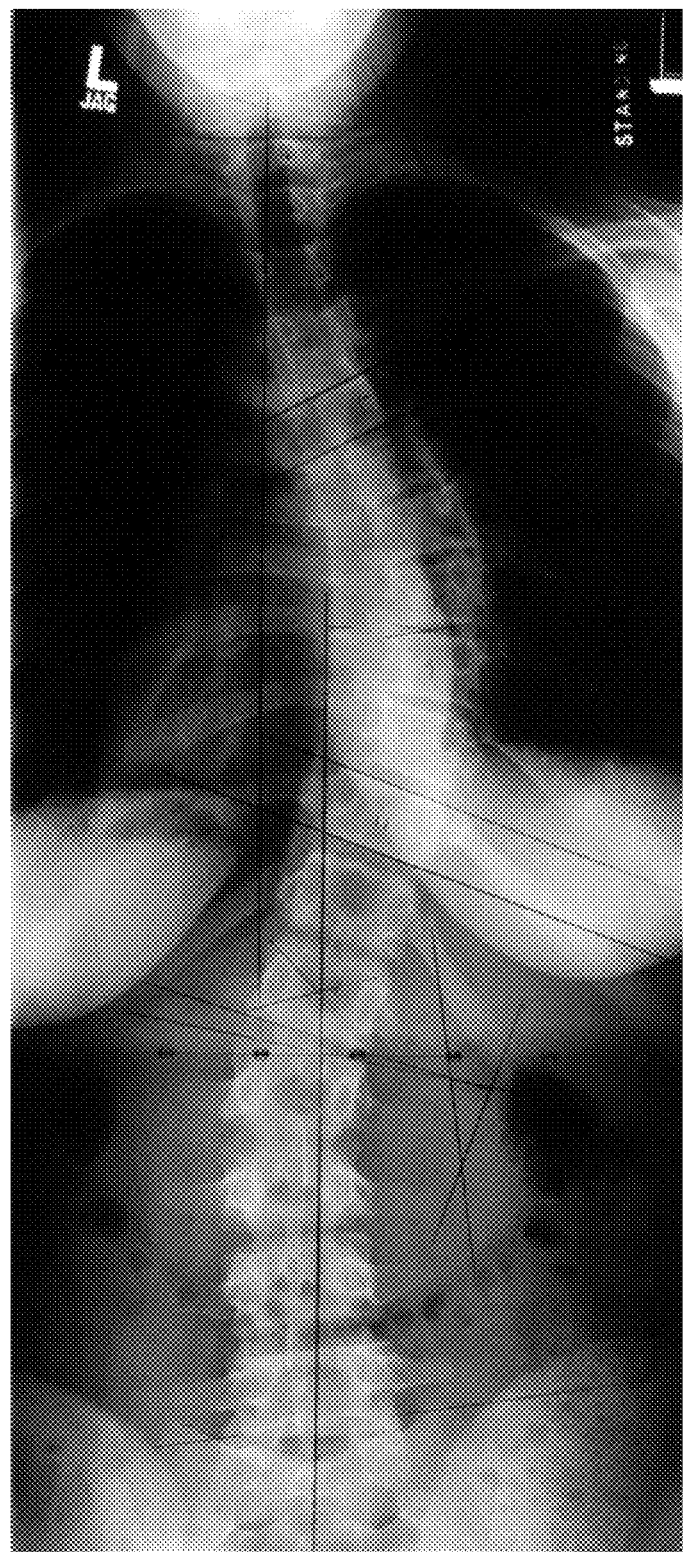
FIG. 3A. Idopathic scoliosis in a representative proband from the 52 family set. Standing posteroanterior radiograph reveals a right thoracic curve in an otherwise healthy adolescent female.
Figure 3B:
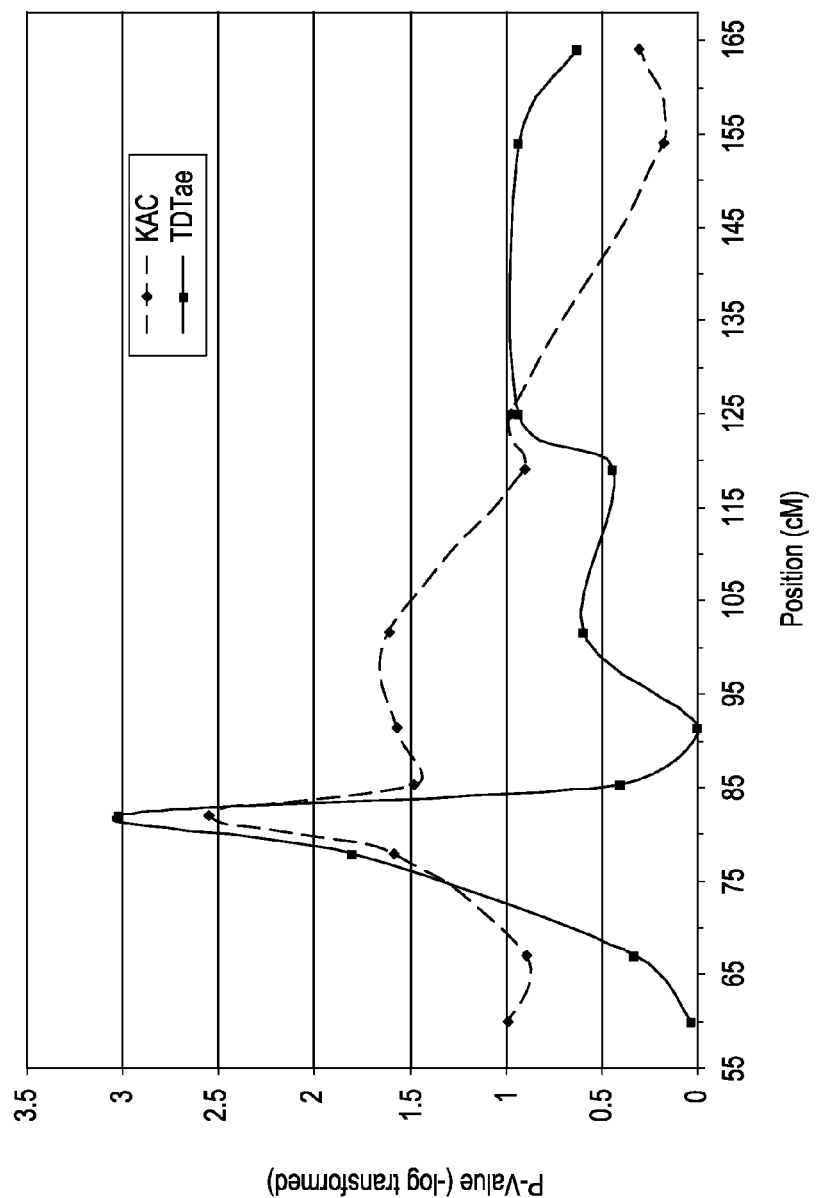
FIG. 3B. Analyses of linkage and transmission disequilibrium for 8q microsatellite loci in 52 IS families.

These results were compared to published findings[3-7] by testing linkage between IS and microsatellite loci in 52 additional multiplex families with 123 affected individuals (FIG. 3a). A region of chromosome 8q was analyzed because of the uncertainty in inheritance model and penetrance for IS. Genetic-model-free methods were used to find likely target loci using "affecteds-only" analyses. This revealed positive evidence for linkage between IS and chromosome 8q loci (maximum LOD=2.77; P=0.0028 at D8S1136; FIG. 3b). Tests of transmission disequilibrium unexpectedly revealed some evidence of association between IS and both D8S1136 (TDTae P=0.001, FIG. 3b), and with the next proximal marker, D8S1113 (TDTae P=0.016), although the latter result was not significant after correction for multiple tests.

FIG. 3a. Idiopathic scoliosis in a representative proband from the 52 family set. Standing posteroanterior radiograph reveals a right thoracic curve in an otherwise healthy adolescent female. 3b. Analyses of linkage and transmission disequilibrium for 8q microsatellite loci in 52 IS families. Polymorphic microsatellites spaced at 5-10 cM were genotyped in all members of the 52 families. The method of Kong and Cox was used to compute linkage (dashed line), and family-based association was measured using the transmission disequilibrium test allowing for errors (TDTae) (solid line). For reporting consistency results are shown as P-values (−log transformed) versus centimorgan position for the two methods.

Based on these results, candidate genes in the 4 cM region between D8S1113 and D8S1136 were investigated. One of these was the chromodomain helicase DNA binding protein 7 (CHD7) gene. Missense, stop, and splicing mutations within coding exons of CHD7 have been identified in 60% of patients with the syndrome of coloboma, choanal atresia, ear malformations and deafness, cardiac defects, and growth delay (CHARGE). Infant mortality in CHARGE syndrome is high, but life expectancy has improved as the epidemiology has become better understood[9-12]. In surviving individuals a high prevalence (over 60%) of later-onset scoliosis was recently reported in a series of adolescent and adult CHARGE syndrome patients[13]. Given this, it was determined whether milder variants in CHD7 could underly IS susceptibility. To test this hypothesis, a fine-mapping study in the region of CHD7 was performed. In the first analysis, 15 SNPs evenly spaced throughout the CHD7 genes were genotyped in the 53 pedigrees including family IS14. Tests of transmission disequilibrium between parental controls and affected offspring revealed strong evidence of association with IS for 11 of the 15 SNPs, which was supported by follow-up analysis of eight additional SNPs in the region. Examination of all 23 SNPs revealed a peak of association encompassing exons 2-4, with the strongest evidence obtained for SNP marker 11 (rs1038351; P=0.00018) (FIG. 4a and Table 1).

FIG. 4. (4A) The CHD7 genomic region is shown above (4A) with exons indicated in blue and intronic conserved sequence blocks shown in red. (4B) Plot of linkage and transmission disequilibrium P-values for 23 SNPs in the CHD7 gene. $-\log_{10}$ P values are plotted along the Y axis versus physical position along the X axis for each SNP. The TDTAE method is more significant than the ASP method for markers in a region of high-pair wise LD as expected, given that the TDT method was originally developed to increase evidence for linkage when marker and trait loci are in high LD (13, 14). (C) Graphical representation of the pair-wise linkage disequilibrium ($\Delta^2$) values for all 23 SNPs. In this figure, pairs of markers with larger $\Delta^2$ values (close to or equal to 1, indicating complete LD) are denoted in red, while pairs with smaller $\Delta^2$ values (closer to or equal to 0, indicating linkage equilibrium) are denoted in blue. (A), (B), and (C) have been aligned so that results for each of the markers correspond between the three figures.

Table 1. Results of two point analyses for the 23 SNPs in the CHD7 gene. Each locus and the corresponding overtransmitted allele are shown. Associated P values are shown for the ASP method measuring linkage, and the TDTae and HRR methods measuring family-based association. The TDTae method was found to be more significant than the ASP method for markers in a region of high-pair wise LD as expected, given that the TDT method was originally developed to increase evidence for linkage when marker and trait loci are in high LD (10, 25). One single locus TDT statistic, for rs1038351 (Position=10.435 cM) was significant at the 5% level after correction for multiple testing using the FDR method. Two point genotype relative risks for each locus are shown in which we assumed a log-additive model of inheritance for the disease. The values presented in the table are maximum likelihood estimates of these values for each of the 23 SNPs. In this analysis the GRR for the homozygous genotype was constrained to be the square of the GRR for the heterozygote genotype, making our statistic equivalent to the original TDT statistic (10) when both parents are genotyped.

tion with IS susceptibility these exons and flanking regions in 25 affected probands and 44 parental controls were resequenced. This revealed two rare coding SNPs, one of which predicted a nonsynonymous change in parental controls, but this was not transmitted to affected offspring. Two previously described intronic SNPs (rs7836586 and rs4540437)[9], were also identified but an obvious function to the transmitted or non-transmitted alleles was not ascribed.

Table 2. Polymorphisms observed by resequencing in 25 IS affected cases and 44 parental controls. Variant observed in the CHD7 mRNA or predicted protein is shown. Genotype frequencies are shown for the total set of resequenced individuals without distinguishing related versus unrelated chromosomes. However, we note that the "unknown" SNP 2 was observed twice, in two unrelated controls, whereas the "unknown" SNP 3 was observed in 4 related cases=1 independent chromosome (denoted by *).

TABLE 1

Results of two point analyses for the 23 SNPs in the CHD7 gene.

| SNP | Location | Locus | ASP LOD | Over-transmitted allele | Associated P value | | | Genotype relative risks | |
|---|---|---|---|---|---|---|---|---|---|
| | | | | | ASP | HHRR | TDTae | $R_1$ | $R_2$ |
| 1 | 61,758,225 | rs4738813 | 0.988 | C | 0.016 | 0.039 | 0.009 | 1.900 | 3.609 |
| 2 | 61,760,363 | rs12544305 | 1.461 | G | 0.005 | 0.004 | 0.002 | 2.373 | 5.627 |
| 3 | 61,777,438 | rs9643371 | 1.912 | T | 0.002 | 0.006 | 7E−04 | 2.478 | 6.139 |
| 4 | 61,781,267 | rs1017861 | 0.584 | G | 0.050 | 0.008 | 0.002 | 2.084 | 4.342 |
| 5 | 61,811,105 | rs13256023 | 0.000 | T | 0.500 | 0.184 | 1.000 | 1.000 | 1.000 |
| 6 | 61,814,698 | rs4288413 | 0.071 | A | 0.284 | 0.046 | 0.030 | 1.755 | 3.079 |
| 7 | 61,820,387 | rs7000766 | 2.718 | G | 2E− | 0.003 | 5E−04 | 2.701 | 7.294 |
| 8 | 61,824,902 | hcv148921 | 1.084 | A | 0.013 | 0.008 | 8E−04 | 2.196 | 4.82 |
| 9 | 61,829,834 | rs1483207 | 1.578 | G | 0.004 | 0.486 | 0.007 | 2.222 | 4.933 |
| 10 | 61,830,452 | rs1483208 | 1.353 | A | 0.006 | 0.002 | 0.003 | 2.284 | 5.216 |
| 11 | 61,832,862 | rs1038351 | 2.145 | T | 8E− | 0.004 | 2E−04 | 3.059 | 9.355 |
| 12 | 61,835,069 | rs7843033 | 2.089 | C | 1E− | 0.002 | 2E−04 | 2.994 | 8.961 |
| 13 | 61,845,746, | rs7002806 | 1.857 | T | 0.002 | 0.013 | 0.009 | 2.049 | 4.200 |
| 14 | 61,847,748 | rs7842389 | 2.491 | T | 4E− | 0.003 | 0.001 | 2.518 | 6.341 |
| 15 | 61,853,914 | rs7017676 | 1.197 | A | 0.009 | 7E−04 | 3E−04 | 2.860 | 8.182 |
| 16 | 61,858,259 | hcv509505 | 0.712 | G | 0.035 | 1E−03 | 8E−04 | 2.455 | 6.028 |
| 17 | 61,862,485 | rs4392940 | 2.269 | A | 6E− | 0.002 | 3E−04 | 2.909 | 8.460 |
| 18 | 61,863,611 | rs4237036 | 1.242 | T | 0.008 | 0.002 | 0.002 | 2.340 | 5.476 |
| 19 | 61,866,609 | rs13280978 | 1.354 | T | 0.006 | 0.003 | 0.004 | 2.105 | 4.431 |
| 20 | 61,871,613 | rs4301480 | 1.570 | A | 0.004 | 0.001 | 0.003 | 2.498 | 6.240 |
| 21 | 61,874,997 | rs10957159 | 0.000 | G | 0.500 | 0.084 | 1.000 | 1.000 | 1.000 |
| 22 | 61,889,433 | rs10092214 | 0.940 | A | 0.019 | 0.500 | 0.434 | 1.181 | 1.395 |
| 23 | 61,926,943 | rs3763591 | 0.800 | T | 0.027 | 0.500 | 0.288 | 1.289 | 1.660 |

Figure 5:
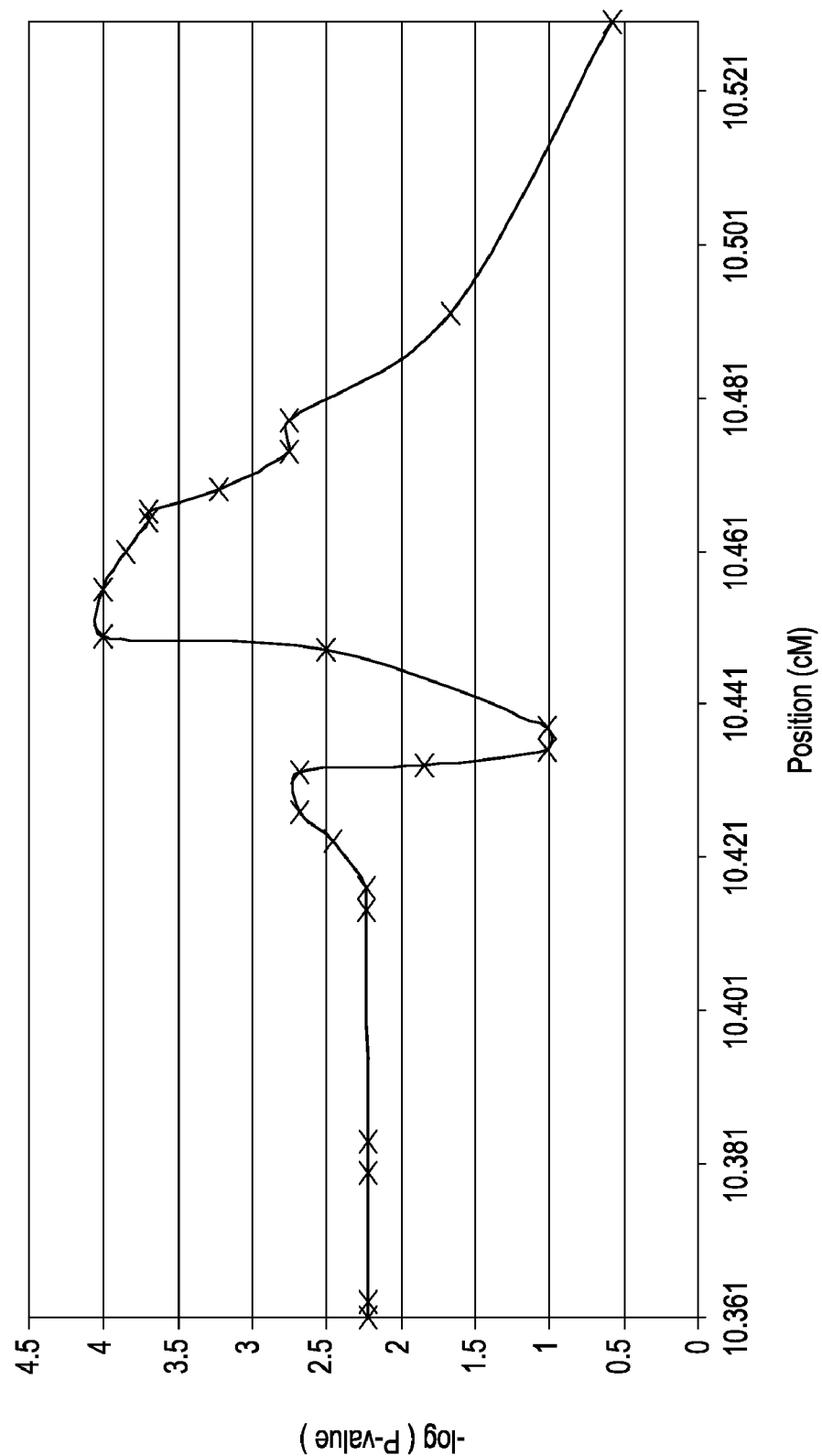
FIG. 5 shows maximum multi-locus TDT results for each set of four SNPs. For SNPs that appear in more than one set of overlapping windows, with an average of the log-transformed P-values for the two maximum multi-locus TDT statistics. P-values were computed using a bootstrap sample of 50,000.

Two point LOD score analysis also produced supporting evidence of linkage (maximum LOD=2.72, P=2.0×10−4 for SNP marker 7, rs7000766). Multi-locus analyses revealed significant overtransmission of overlapping haplotypes, with strongest results for haplotypes containing SNPs 14-19 (FIG. 5). Pair-wise estimates of linkage disequilibrium (LD) for all 23 SNPs revealed highest LD within the region defined by SNPs 15-19 (FIG. 4c). Evaluating the multi-locus data altogether therefore provided strongest evidence for association with IS in a region encompassing SNPs 14-19.

The CHD7 gene spans 188 kb and contains one noncoding (exon 1) and 37 coding exons (FIG. 4a). The SNP loci we found associated with IS susceptibility are clearly contained within a ~116 kb region encompassing exons 2-4 of the CHD7 gene. A search for potential functional elements in this region was conducted and extended out to exon 7 by comparing publicly available reference sequences across vertebrate species. This identified 16 blocks of relatively high sequence conservation, with coding exons 2-7 comprising six of these blocks (FIG. 4a). To identify variants underlying the associa-

TABLE 2

Polymorphisms observed by resequencing in 25 IS affected cases and 44 parental controls.

| SNP | Exon/Intron | Variant | dbSNP | Genotype | Frequency |
|---|---|---|---|---|---|
| 1 | 2 | M340V | Unknown | AA | 67 |
| | | | | AG | 2 |
| | | | | GG | 0 |
| 2 | 2 | P544P | Unknown | CC | 64 |
| | | | | CG | 4* |
| | | | | GG | 0 |
| 3 | 2 | c. 1665 + 34 | rs7836586 | AA | 55 |
| | | | | AG | 13 |
| | | | | GG | 0 |
| 4 | 2 | c. 1666 − 3238 | rs4738824 | AA | 0 |
| | | | | AG | 13 |
| | | | | GG | 54 |
| 5 | 4 | c. 2238 + 39 | rs4540437 | AA | 59 |
| | | | | AG | 13 |
| | | | | GG | 00 |

Next, the ten remaining conserved sequence blocks were searched in silico for similarity to known functional elements were searched. One region, sequence block three, was found to harbor the highest density of predicted transcription factor binding sites. In particular, thirty independent consensus sequences for caudal-type (cdxA) sites were predicted in the ~700 base pairs comprising conserved block 3.

Table 3 Analyses of conserved sequence blocks in the CHD7 gene. Locations of DNA sequence conservation as identified using the UCSC conservation track are shown. The two most abundant transcription factor binding sites, as predicted by TFSEARCH, are shown along with the number of independent consensus sequences identified for each. For block 8, no TF binding sites were predicted more than once other than Cdx.

TABLE 3

Analyses of conserved sequence blocks in the CHD7 gene.

| Block | Location (bp) | Size (bp) | Predicted TF binding sites | Number of sites |
|---|---|---|---|---|
| 1 | 61,844,311-61,844,737 | 426 | Cdx | 11 |
|   |   |   | SRY | 5 |
| 2 | 61,845,377-61,845,721 | 344 | Cdx | 7 |
|   |   |   | Nkx-2 | 5 |
| 3 | 61,852,850-61,853,569 | 719 | Cdx | 30 |
|   |   |   | SRY, GATA-n | 7 |
| 4 | 61,856,975-61,857,402 | 427 | Cdx | 8 |
|   |   |   | SRY | 3 |
| 5 | 61,858,961-61,859,577 | 616 | Cdx | 15 |
|   |   |   | SRY, Oct-1 | 6 |
| 6 | 61,860,005-61,860,527 | 522 | Cdx | 19 |
|   |   |   | Nkx-2, Oct-1 | 3 |
| 7 | 61,867,600-61,868,850 | 1,250 | Cdx | 30 |
|   |   |   | SRY, GATA-n, C/EBPn | 8 |
| 8 | 61,875,850-61,876,200 | 350 | Cdx | 14 |
| 9 | 61,878,250-61,878,500 | 250 | Cdx | 6 |
|   |   |   | Nkx-2 | 3 |
| 10 | 61,882,400-61,883,120 | 720 | Cdx | 21 |
|   |   |   | SRY | 6 |

The caudal homeobox transcription factors are required for anterior/posterior positional cues and appropriate embryonic axial development in model organisms14-15. Resequencing this block in cases and parental controls as before revealed a polymorphism, rs4738824, which predicts disruption of a possible binding site for caudal-type (cdx) homeodomain-containing transcription factors. Specifically, in this polymorphism an A nucleotide that appears to be perfectly conserved across nine vertebrate species is replaced by a G nucleotide. We analyzed SNP rs4738824 in the remaining families and found significant overtransmission of the G allele predicted to disrupt cdx binding (TDTae P=0.005). Furthermore, the set of consecutive SNP markers 14-19 all displayed high pair-wise $\Delta^2$ values (>0.6) with this SNP, which lies between the original SNPs 14 and 15 (full results not shown). The convergence of linkage, linkage disequilibrium, and sequence conservation surrounding SNP rs4738824 therefore strongly suggested a functional role for this polymorphism that could influence IS susceptibility. As a preliminary measure of this, we estimated genotype relative risks (GRRs) for SNP rs4738824 and the original 23 genotyped SNPs. Our results predicted heterozygote relative risks ranging from 1.90 to 3.06, with a value of 2.4 for rs4738824 (Table 1).

Idiopathic forms of scoliosis have been described for centuries, but the aetiology has remained a clinical conundrum. Our results are the first description of a responsible gene and provide an initial insight into underlying disease mechanisms. Haploinsufficiency of CHD7 protein during embryogenesis has been proposed to explain the CHARGE syndrome in the presence of CHD7 coding mutations. We likewise hypothesize that a relative reduction of functional CHD7 in the postnatal period, particularly during the adolescent growth spurt, may disrupt normal growth patterns and predispose to spinal deformity. This may be mediated at the transcriptional level by interaction of CHD7 cis-acting elements with factors such as cdx. In this context, SNP rs4738824 and possibly other functional variants that are in linkage disequilibrium with this SNP may alter CHD7 expression. Further studies of CHD7-mediated pathways may help to elucidate the complex mechanisms responsible for IS susceptibility.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Abecasis, G. R., Cookson, W. O. Bioinformatics 16, 182-183 (2000).
Barral, S., Haynes, C., Levenstien, M. A., Gordon, D. BMC Genet 6, S150 (2005).
Bashiardes, S. et al. Hum. Genet. 115, 81-89 (2004).
Benjamini, Y., Drai, D., Elmer, G., Kafkafi, N., Golani, I. Behav Brain Res 125, 279-284 (2001).
Benjamini, Y., Hochberg, Y. J Roy Statist Soc B 57, 289-300 (1995).
Boyles A. L. et al., Hum Hered 59, 220-227 (2005).
Chan, V. et al. Amer. J. Hum. Genet. 71, 401-406 (2002).
Clayton, D. Am J Hum Genet 65, 1170-1177 (1999).
de Kok, J. B., Wiegerinck, E. T., Giesendorf, B. A., Swinkels, D. W. Hum Mutat. 19, 554-559 (2002).
Doyle, C. & Blake, K. Amer. J. Med. Genet. 133A, 340-343 (2005).
Emery, A. E. H. & Rimoin, D. L. Principles and Practice of Molecular Genetics (Churchill Livingstone, N.Y., 1990)
Falk, C. T., Rubinstein, P. Ann Hum Genet 51, 227-233 (1987).
Fisher, R. A. The Design of Experiments (Oliver and Boyd, Edinburgh, 1960).
Gordon et al. Eur J Hum Genet 12, 752-761 (2004).
Gordon, D., Heath, S. C., Liu, X., Ott, J. Am J Hum Genet 69, 371-380 (2001).
Heinemeyer, T., Wingender, E., Reuter, I., Hermjakob, H., Kel A. E. et al. Nucleic Acids Res. 26, 364-370 (1998).
Herring, J. A. Tachdjian's Pediatric Orthopaedics (W.B. Saunders, Philadelphia, 2002).
Hill W. G., Weir, B. S. Am J Hum Genet 54, 705-714 (1994).
Jongmans, M. C. et al. J. Med. Genet. 43, 306-314 (2006).
Justice, C. M., Miller, N. H., Marosy, B., Zhang, J. & Wilson, A. F. Spine 28, 589-594 (2003).
Kong, A., Cox, N.J. Am J Hum Genet 61, 1179-1188 (1997).
Kruglyak, L., Daly, M. J., Reeve-Daly, M. P., Lander, E. S. Am J Hum Genet 58, 1347-1363 (1996).
Lalani, S. R. et al. Am. J. Hum. Genet. 78, 303-314 (2006).
Lathrop, G. M., Lalouel, J. M., Julier, C., Ott, J. Proc Natl Acad Sci USA 81, 3443-3446 (1984).
Livak, K. J. Genet. Anal. 14, 143-149 (1999).
Lohnes, D. Bioessays 25, 971-980 (2003).
Miller N. H. et al. Spine 30, 1181-1187 (2005).
Mukhopadhyay, N., Almasy, L., Schroeder, M., Mulvihill, W. P., Weeks, D. E. Bioinformatics 21, 2556-2557 (2005).
Salehi, L. B. et al. Hum. Genet. 111, 401-404 (2002).
Sanlaville, D. et al. J. Med. Genet. 43, 211-217 (2006).
Schaid, D. J., Sommer, S. S. Am J Hum Genet 53, 1114-1126 (1993).
Spielman, R. S., McGinnis, R. E., Ewens, W. J. Am J Hum Genet 52, 506-516 (1993).
Subramanian, V., Meyer, B. I. & Gruss, P. Cell 83, 641-653 (1995).
Terwilliger, J. D. Am J Hum Genet 56, 777-787 (1995).
Terwilliger, J. D., Ott, J. Hum Hered 42, 337-346 (1992).
Vissers, L. E. et al. Nat. Genet. 36, 955-957 (2004).
Wise, C. A. et al. Spine 25, 2372-2380 (2000).

What is claimed is:

1. A method for determining if a human patient has a predisposition to idiopathic scoliosis comprising: obtaining a nucleic acid sample from the patient; assaying the sample to identify the nucleotide present at single nucleotide polymorphism rs4738824; and determining that the patient has a predisposition to idiopathic scoliosis when there is at least one G allele present at single nucleotide polymorphism rs4738824 relative to a human patient that has two A alleles present at single nucleotide polymorphism rs4738824.

2. The method of claim 1, wherein assaying the sample to identify the nucleotide present at single nucleotide polymorphism rs4738824 comprises amplifying the chromodomain helicase DNA binding protein 7 gene.

3. The method of claim 1, wherein assaying the sample to identify the nucleotide present at single nucleotide polymorphism rs4738824 comprises performing fluorescence in situ hybridization, nuclease protection assay, gel-shift assay, Southern blot analysis, anchor PCR, RACE PCR, ligase chain reaction (LCR), in situ hybridization, immunoprecipitation, immunohistochemistry, Genetic Bit Analysis, primer guided nucleotide incorporation, oligonucleotide ligation assay (OLA) and protein truncation test (PTT), DNA sequencing or RNA sequencing.

4. The method of claim 1, wherein an amplicon is used to detect the single nucleotide polymorphism.

5. The method of claim 1, wherein the single nucleotide polymorphism is identified by PCR amplification of the chromodomain helicase DNA binding protein 7 gene and nested PCR of overlapping constituent fragments of the chromodomain helicase DNA binding protein 7 gene at the single nucleotide polymorphism.

6. The method of claim 1, wherein the sample comprises a body fluid or a tissue.

7. The method of claim 1, wherein the sample is sequenced at the DNA or RNA level to identify the single nucleotide polymorphism.

8. A method of diagnosing a susceptibility to idiopathic scoliosis in a human patient comprising: obtaining a nucleic acid sample from the patient; assaying the sample to identify the nucleotide present at single nucleotide polymorphism rs4738824; and diagnosing the human patient as being susceptible to idiopathic scoliosis when there is at least one G allele present at single nucleotide polymorphism rs4738824 relative to a human patient that has two A alleles present at single nucleotide polymorphism rs4738824.

* * * * *

UNITED STATES PATENT AND TRADEMARK OFFICE
CERTIFICATE OF CORRECTION

| | | |
|---|---|---|
| PATENT NO. | : 7,655,403 B2 | Page 1 of 1 |
| APPLICATION NO. | : 11/566215 | |
| DATED | : February 2, 2010 | |
| INVENTOR(S) | : Carol Wise | |

It is certified that error appears in the above-identified patent and that said Letters Patent is hereby corrected as shown below:

Col. 2, line 20
Replace "acid sample obtained from the patient and determining" with --acid sample from the patient and determining--

Col. 3, line 36
Replace "one or more containers comprises a pair" with --one or more containers comprising a pair--

Col. 16, lines 34
Replace "Given this,it was" with --Given this, it was--

Col. 19, lines 2-3
Replace "searched in silico for similarity to known funtional elements were searched." with --searched in silico for similarity to know functional elements.--

Signed and Sealed this
Twenty-first Day of June, 2011

David J. Kappos
*Director of the United States Patent and Trademark Office*

SEQUENCE LISTING

<160> NUMBER OF SEQ ID NOS: 1

<210> SEQ ID NO 1
<211> LENGTH: 10469
<212> TYPE: DNA
<213> ORGANISM: homo sapiens

<400> SEQUENCE: 1

```
gcggcggcgg cagcggcggc ggcggcggcg gcgcgggggt tgagtcgtgg tggtgcggac        60
gcgctcgtgc tcgggaacta tcggattaaa cttgaatcga gtgaaattac acaaaggagc       120
gccgcggagg aggcggcccg gggacccgga caccctgaaa ctcaccagag acccgttcgc       180
ccccggccaa ctccgtgccc gtggattcag cccccctggcc gcagctgccg agccaactcc      240
ggagcccgct ctgcgttttg ttttcccctc ggcactaggc agcggaggag cccgaccgac       300
ccggacctat atccagactt tgcctgacac tgcagggtcc aagagaatta aagaaatatg       360
gaatgacatg aagaagatta gttaaggatt ataggctttg agggcaaaca cctcagtgaa       420
gtgaagcaca ggcaagctcc tgagctgtgg tttggaggag ccgtgtgttg gaagaagatg       480
gcagatccag gaatgatgag tcttttttggc gaggatggga atatttttcag tgaaggtctt      540
```

-continued

| | |
|---|---|
| gaaggcctcg gagaatgtgg ttacccggaa atccagtaa atcctatggg tcagcaaatg | 600 |
| ccaatagacc aaggctttgc ctctttacag ccatcccttc atcatccttc aactaatcaa | 660 |
| aatcaaacaa agctgacaca ttttgatcac tataatcagt atgaacaaca aaagatgcat | 720 |
| ctgatggatc agccgaacag aatgatgagc aacacccctg ggaacggact cgcgtctccg | 780 |
| cactcgcagt atcacacccc tcccgttcct caggtgcccc atggtggcag tggtggcgt | 840 |
| cagatgggtg tctaccctgg catgcagaat gagaggcatg gcaatcctt tgtggacagc | 900 |
| agctccatgt gggggcccag ggctgttcag gtaccagacc agatacgagc cccctaccag | 960 |
| cagcagcagc cacagccgca gccaccgcag ccggctccgt cggggccccc tgcacagggc | 1020 |
| caccctcagc acatgcagca gatgggcagc tatatggcac gtggggattt ttccatgcag | 1080 |
| cagcatggtc agccacagca gaggatgagc cagttttccc aaggccaaga gggcctcaat | 1140 |
| cagggaaatc ctttattgc cacctcagga cctggccact tgtcccacgt gccccagcag | 1200 |
| agtcccagca tggcaccttc cttgcgtcac tcggtgcagc agttccatca ccacccctct | 1260 |
| actgctctcc atggagaatc cgttgcccac agtcccagat tctccccgaa tcctccccaa | 1320 |
| caaggggctg ttaggccgca aacccttaac tttagttctc ggagccagac agtcccctct | 1380 |
| cctactataa acaactcagg gcagtattct cgatatcctt acagtaacct aaatcaggga | 1440 |
| ttagttaaca atacagggat gaatcaaaat ttaggcctta caataatac tccaatgaat | 1500 |
| cagtccgtac caagatacc caatgctgta ggattcccat caaacagtgg tcaaggacta | 1560 |
| atgcaccagc agcccatcca ccccagtggc tcacttaacc aaatgaacac acaaactatg | 1620 |
| catccttcac agcctcaggg aacttatgcc tctccacctc ccatgtcacc catgaaagca | 1680 |
| atgagtaatc cagcaggcac tcctcctcca caagtcaggc cgggaagtgc tgggatacca | 1740 |
| atggaagttg gcagttatcc aaatatgccc catcctcagc catctcacca gcccctggt | 1800 |
| gccatgggaa tcgacagag gaatatgggc cccagaaaca tgcagcagtc tcgtccattt | 1860 |
| ataggcatgt cctcggcacc aagggaattg actgggcaca tgaggccaaa tggttgtcct | 1920 |
| ggtgttggcc ttggagaccc acaagcaatc caggaacgac tgatacctgg ccaacaacat | 1980 |
| cctggtcaac agccatcttt tcagcagttg ccaacctgtc ctccactgca gcctcacccg | 2040 |
| ggcttgcacc accagtcttc acctccacac cctcatcacc agccttgggc acagctccac | 2100 |
| ccatcacccc agaacacccc gcagaaagtg cctgtgcatc agcattcccc gtcggagccc | 2160 |
| tttctagaga aaccagtgcc ggatatgact caggttagtg gaccgaatgc tcagctagtg | 2220 |
| aagagtgatg attacctgcc atcaatagaa cagcagccac aacaaaagaa gaagaaaaag | 2280 |
| aaaaacaacc acattgtagc agaggatccc agtaaaggtt ttggtaaaga tgacttccct | 2340 |
| ggtggggtag ataaccaaga actaaatagg aactcactgg atgggtccca agaagaaaaa | 2400 |
| aagaaaaaga aaggtcaaa ggcaaaaaaa gacccgaagg aaccgaaaga acccaaggag | 2460 |
| aaaaaagagc ccaggaacc caagaccccg aaagccccta agattcccaa agagccaaag | 2520 |
| gaaaagaaag caaaaactgc cacgccaaaa cccaaatcca gcaaaaagtc aagtaataag | 2580 |
| aaacctgact cagaagcaag tgctttgaag aaaaaggtca acaagggaaa aacagaaggt | 2640 |
| tctgaaaatt cagacttaga caaaacaccc ccaccatctc ctcctcctga agaagatgag | 2700 |
| gacccaggtg ttcagaagag acggtccagc agacaggtga agaaaagcg ctacactgaa | 2760 |
| gacctggagt tcaagatttc tgatgaggag gcagatgatg cagatgctgc tgggagggat | 2820 |
| tccccctcca acacctccca gtcagaacag caggaatctg ttgatgcaga aggcccagtg | 2880 |
| gtagaaaaaa ttatgagcag tcgttcagta aaaaagcaga aggaatctgg agaggaggta | 2940 |

```
gaaattgagg aattctatgt gaaatacaaa aacttctctt atcttcattg tcagtgggca   3000
tctatagaag atctggaaaa agataagaga attcagcaaa aaattaaacg atttaaggca   3060
aagcagggcc agaacaagtt cctttcagag attgaggatg agcttttaa tccagattat    3120 gtggaggttg accggataat ggactttgca cgtagcacag atgaccgggg agagcctgtg   3180
actcactatc tggtgaagtg gtgttcactt ccttatgaag acagcacgtg ggagcggagg   3240
caggacatag atcaagcaaa gatcgaggag tttgagaaac taatgtccag ggagccggaa   3300
acagagcgtg tggagcgacc tcctgctgat gattggaaga atcggagag ttccagggag    3360 tataaaaaca ataacaaact cagggaatac cagttggagg gagtaaactg gctactttc    3420 aattggtaca acatgcgaaa ctgcatttta gcagatgaaa tgggtttggg aaaaactatc   3480
cagtccatta catttctcta tgagatatat ttgaaaggaa tccatggccc ttttttagta   3540
attgccccat tgtccacaat ccccaactgg gaaagggaat tccgaacctg gacagagttg   3600
aacgtggttg tgtatcatgg gagtcaagct agtcgtcgga ccattcagtt gtatgaaatg   3660
tacttcaaag atccccaggg tcgagtgata aaggggtcct ataagtttca tgccatcatc   3720
actacatttg agatgatttt gactgattgt cctgagctgc ggaatattcc atggcgctgt   3780
gtagtcattg atgaagccca caggctgaag aacaggaact gcaagctgtt ggagggactc   3840
aagatgatgg acttggaaca caaagtgctg ctgacgggaa ccccactcca gaacactgtg   3900
gaagaactct tcagcttgct tcatttcttg gaaccaagtc gcttccttc agaaaccaca    3960 tttatgcaag aatttggtga tctaaaaaca gaagagcagg tgcaaaaact tcaagctatt   4020
ctaaagccaa tgatgttgag acgtctcaaa gaggatgtag aaaagaactt ggcccccaaa   4080
gaagaaacta ttattgaagt tgagctaaca aacattcaga gaaatattta ccgagccatc   4140
cttgagaaga atttcacatt tcttttccaaa ggcggtggtc aagctaacgt acctaaccta  4200
ttaaacacta tgatggaatt gcggaagtgc tgcaatcatc cgtaccttat caatggtgct   4260
gaagagaaaa ttttggaaga gtttaaagaa acacacaatg cagagtctcc agattttcag   4320
ctccaggcaa tgatccaggc tgctggcaag ctagtgctga ttgacaagct gctgccaaaa   4380
ctgaaggctg gtggccacag ggtgcttatc ttttcccaga tggtgcgctg cttggacata   4440
ctggaagact acctcattca aagacggtac ccatatgaaa ggatcgacgg ccgagtaaga   4500
ggcaacctcc gccaggcagc tatcgacaga ttctccaaac ctgattctga taggtttgtt   4560
ttcctcctgt gtacaagggc aggaggttta ggcattaacc tcactgctgc tgatacctgc   4620
atcatctttg attcagactg gaatccccaa aatgacctcc aggctcaggc tagatgtcat   4680
agaataggac agagcaaatc tgtgaaaatc tacaggctga ttacaagaaa ttcctatgaa   4740
agggaaatgt tcgacaaggc tagtttgaaa ctgggcctgg ataaagctgt gctacagtct   4800
atgagtggaa gagaaaatgc taccaatggg gtacaacagc tttccaagaa agaaatagag   4860
gatcttctac gaaaagggc ctatggtgca ctcatggatg aggaggatga agggtctaaa    4920
ttctgtgaag aagatattga tcagatcctc ctacgtcgaa cccacaccat taccattgag   4980
tcagaaggga aggttccac atttgctaag gccagttttg ttgcatctgg aaataggaca    5040
gatatttcct tggatgatcc aaatttctgg caaaagtggg ctaagaaggc tgaattggat   5100
attgatgcct taaatgggag gaacaacctg gttattgata ctccaagagt gagaaagcag   5160
accaggctct acagtgcagt gaaggaagat gagctgatgg agttctcaga cttggaaagt   5220
gattctgaag aaaagcccctg tgcaaagcca cggcgtcccc aggataagtc acagggctat   5280
```

```
gcaaggagtg aatgtttcag ggtggagaag aatctgcttg tctatggttg gggacggtgg    5340
acagacattc tttcccacgg acgctataaa cgccaactca ctgagcaaga tgtagaaacc    5400
atctgcagaa ccatcctggt gtactgtctt aatcattaca aagggatgaa gaatatcaaa    5460
agcttcatct gggatctgat cacacccaca gcggatggcc agactcgagc cttggtcaac    5520
cattccggtt tgtcagctcc tgtgccaagg ggaaggaagg gaaagaaggt gaaagcccag    5580
agcacacagc cggtggtgca ggatgccgac tggctggcca gctgcaaccc agatgccctg    5640
ttccaggagg acagctacaa gaaacacctg aagcatcact gtaacaaggt cctgctgcgt    5700
gtccgcatgc tgtactacct aagacaagaa gtgataggag accaggcgga taagatctta    5760
gagggtgctg actcaagtga agccgatgtg tggatccctg aacctttcca tgctgaagtt    5820
cctgcagatt ggtgggataa ggaagcagac aaatccctct taattggagt gttcaaacat    5880
ggctatgaga agtacaactc catgcgagct gaccccgcgc tgtgctttct ggaacgagtc    5940
ggtatgcctg atgccaaggc catagctgcc gagcaaagag aacagacat gctagcagat    6000 ggtggtgacg ggggagaatt tgatagagaa gatgaagacc cagaatataa accaaccaga    6060
acaccgttca aagatgaaat agatgaattt gcaaattctc cttcagagga taaggaagaa    6120
tccatggaaa tacatgccac aggcaagcac agtgagagta atgctgagtt aggccaactt    6180
tactggccta acacttcaac cctgactaca cgtctgcgcc ggctcattac tgcctatcag    6240
cgcagctata aaaggcaaca gatgaggcaa gaggccctaa tgaagactga ccggcgcaga    6300
cggcggcctc gagaggaagt gagagctctg aagcggaaa gggaagctat tatatctgag    6360
aagcggcaaa agtggacaag aagagaagag gctgattttt accgtgtggt atccacctt    6420 ggggttattt ttgaccctgt gaaacagcaa tttgactgga accaatttag agcctttgcc    6480
aggcttgaca aaaaatctga tgagagtttg gagaaatact tcagttgttt tgtggccatg    6540
tgtaggcgag tatgtcgaat gcccgtcaag ccagatgatg aaccgcccga cctctcctcc    6600
ataattgagc cgatcacaga ggagcgagcc tctcgaactc tgtaccgcat tgagctgcta    6660
cggaagatcc gcgagcaggt tctccatcac ccccagctgg agagaggct aagctctgc     6720 cagccaagct tggatctgcc agagtggtgg gagtgtggac ggcatgaccg agacttgctg    6780
gttggtgctg ctaaacacgg ggtcagtcgg acggattatc acatcctcaa tgaccctgag    6840
ttatccttct tggatgcaca taaaaacttt gctcaaaaca gaggggcagg taatacatct    6900
tccttgaacc cactggcagt tggatttgtc cagactcctc cagtcatctc atctgctcat    6960
attcaagatg agagggtact ggaacaagcc gaaggcaaag tggaggagcc tgaaaaccca    7020
gctgccaagg agaaatgtga gggcaaagaa gaggaagaag aaaccgatgg cagcgggaag    7080
gagagcaagc aggaatgtga ggcagaggcc agctctgtga aaaatgaact gaaaggtgtt    7140
gaggtcggcg cagacactgg gtccaaatct atttcagaga aaggttccga agaggatgaa    7200
gaggaaaagc tggaggatga cgataagtcg gaagagtctt cccagcccga agcaggagct    7260
gtctctagag ggaagaattt tgatgaagaa agcaatgctt ccatgagcac tgctagagat    7320
gaaacccgag atggattcta catggaggac ggagatcctt cagtagctca gctccttcat    7380
gaaagaacat ttgccttctc gttttggcct aaggatagag taatgataaa ccgcttagac    7440
aacatctgtg aagcagtgtt gaaaggcaaa tggccagtaa ataggcgcca gatgtttgat    7500
ttccaaggcc tcatcccagg ttacacaccc accacagtgg acagcccctt gcagaagagg    7560
agctttgctg agctctccat ggtcggccaa gccagcatta gtgggagtga ggacatcact    7620
acgtctcctc agttgtcaaa ggaagatgcc ctcaacctct ctgtccctcg ccagcggagg    7680
```

```
aggaggagga gaaaaatcga aattgaggcc gaaagagctg ccaagaggcg aaatctcatg   7740
gagatggttg cccagcttcg agagtctcag gtggtctcag aaaatggaca agaaaaagtt   7800
gtagatttat caaaggcctc aagagaggca acaagctcta cctcaaattt ttcatctctt   7860
tcttcaaagt ttatcttgcc taatgtctca acaccagtgt ctgatgcctt taagactcaa   7920
atggaactgc tccaagcagg cctttcgcgc acacccacaa ggcatctcct taatggctcc   7980
ctagtggatg gagagcctcc catgaagagg aggcgnggaa ggaggaaaaa tgtggaggga   8040
cttgatctgc ttttcatgag ccacaaacgg acgtcattga gtgcagagga tgctgaggtg   8100
accaaagctt ttgaagaaga tatagagacc ccaccaacaa gaaacattcc ttctcccgga   8160
cagctggacc cagacacacg gatccctgtt atcaatcttg aagatgggac taggctggtg   8220
ggggaagatg ctcctaaaaa taaggattta gttgaatggc tgaagctgca ccctacttac   8280
actgttgata tgccaagtta tgtaccaaag aatgcagatg tgctgttttc ctcatttcag   8340
aaaccgaaac agaaacgaca tagatgtcga accctaata aattggatat aaacactttg   8400
acaggagaag aaagggtgcc tgttgtcaat aaacgaaatg ggaagaagat gggtggagct   8460
atggcgcctc caatgaagga tctacccagg tggctggaag aaaatcctga atttgcagtt   8520
gctccagact ggactgatat agttaagcag tctggttttg ttcctgagtc gatgtttgac   8580
cgccttctca ctgggcctgt agtgcgggga gagggagcga gcagaagagg aagaaggccc   8640
aaaagtgaga tcgccagagc agccgcggcc gccgctgctg tggcctccac gtcagggatc   8700
aaccctttgc tggtgaacag cctgtttgct ggaatggacc tgacgagcct tcagaatctc   8760
cagaatctcc agtcgctcca gctggcaggc ctcatgggct ccctccagg actggcaaca   8820 gctgccaccg ccggaggcga tgcgaagaac cctgctgctg tgctgcccct gatgctgcca   8880
ggaatggcgg gcctgcccaa cgtgtttggc ttgggcgggc tgttgaataa ccctctgtca   8940
gctgctactg gaaacaccac tactgcttct agtcaaggag aaccggaaga cagcacttca   9000
aaaggagagg agaaaggaaa tgagaatgaa gacgagaaca aagactctga gaaaagcaca   9060
gatgctgttt cggctgctga ctctgcgaat ggatctgttg gtgctgctac tgcccccggct   9120 ggattgccct caaacccgct agccttcaac cctttcctcc tgtccacaat ggccccgggc   9180
ctcttctacc catccatgtt tctacctcca ggactggggg gattgacgct gcctgggttc   9240
ccagcattgg caggacttca gaatgccgtg ggctccagcg aagaaaaggc tgctgacaag   9300
gctgagggag gaccctttaa agatggagag acccttgaag gcagcgatgc cgaggagagc   9360
ctggataaga ctgcagagtc ctccctctta gaagacgaaa tagcacaggg tgaagagcta   9420
gactcacttg atgggggga tgaaatagaa acaatgaaaa tgatgaata accagtacca   9480 gttccagttc aagtgtttaa aacttttgac aagtggtagt cctactgttt acactcacag   9540
ttaatgttca tacctagttt tataagctgt tctgtaacat agtgtagcaa aaaaaaagt   9600 tcaagtcatg ttatacaggt gtgtcaaaag gtatcttggt cattaagtat tgtgcagtgc   9660
attatttatt atccctagga gagatgaaat ttgagaggtg atcatgtctt tttaaggaaa   9720
cttacataat gctctgcttt ttttttttct cttggtacca ttggtattat aataaagagc   9780
aatttgtaac tgagtggcac taatggaaga aagtgctgct caaggaagt atgaagttat   9840 atatttaatt tttttaatttt aattttttaat ttttttgctg tgaaggtcaa gctgaaattt   9900
accatacata tcatacttgc tcatttgttt cccttttga ctgtatgggg gttcccacac   9960
tcgtgcatac acacacatcc atacactctg acaatctcca cgctagtgtg aacgcctctg   10020
```

```
tcccgaggcg cagcaataat aaggcagctg ttgaatgtga agggtccctt tggaaaatta  10080
acctactggg agggttcttg ccagacagaa ctacagttcc attgtctcgt ggtcttgtaa  10140
tgcactggta aaacaaaat aaatagatga ataaataaag agtgagagaa gagagaatca   10200 ggtaccttt ttaaattaaa ggactttgtt actttagcca caaagctaaa acagcattac    10260
ctcagctcta aactagcctt gaagtttaca gacatgactt tgtaaatgta ttgttttct    10320 ttgttgtgat gtcctttat ttttttcttt gaaaactgct atcatgtaag ataaaatgta    10380
aattgctgcc aactgtagta atgatgcttt taataaaagt gacccatgat atgcagagat   10440
gtaaaaaaaa aaaaaaaaa aaaaaaaaa                                     10469
```